United States Patent
Sum et al.

(10) Patent No.: US 7,176,225 B2
(45) Date of Patent: Feb. 13, 2007

(54) OXAZOLE DERIVATIVES OF TETRACYCLINES

(75) Inventors: Phaik-Eng Sum, Pomona, NY (US); David Brian How, Nyack, NY (US); Darrin William Hopper, New York, NY (US); Matthew Douglas Vera, Royersford, PA (US); Joshua James Sabatini, White Plains, NY (US)

(73) Assignee: Wyeth, Madison, NJ (US)

( * ) Notice: Subject to any disclaimer, the term of this patent is extended or adjusted under 35 U.S.C. 154(b) by 33 days.

(21) Appl. No.: 11/007,621

(22) Filed: Dec. 8, 2004

(65) Prior Publication Data
US 2005/0153944 A1   Jul. 14, 2005

Related U.S. Application Data

(60) Provisional application No. 60/584,823, filed on Jul. 1, 2004, provisional application No. 60/527,928, filed on Dec. 8, 2003.

(51) Int. Cl.
*A61K 31/423* (2006.01)
*C07D 263/52* (2006.01)

(52) U.S. Cl. ..................................... 514/375; 548/223
(58) Field of Classification Search ................ 548/223; 514/375
See application file for complete search history.

(56) References Cited

U.S. PATENT DOCUMENTS

| 2,482,055 A | 9/1949 | Duggar |
| 3,007,965 A | 11/1961 | Growich, Jr. et al. |
| 3,043,875 A | 7/1962 | Beereboom et al. |
| 3,148,212 A | 9/1964 | Boothe et al. |
| 3,200,149 A | 8/1965 | Blackwood et al. |
| 3,226,436 A | 12/1965 | Boothe et al. |
| RE26,253 E | 8/1967 | Petisi et al. |
| 3,338,963 A | 8/1967 | Petisi et al. |
| 3,341,585 A | 9/1967 | Bitha et al. |
| 3,360,557 A | 12/1967 | Shu |
| 3,360,561 A | 12/1967 | Zambrano |
| 3,518,306 A | 6/1970 | Martell et al. |
| 5,021,407 A | 6/1991 | Levy |
| 5,494,903 A | 2/1996 | Hlavka et al. |

FOREIGN PATENT DOCUMENTS

| EP | 0582788 A1 | 2/1994 |
| WO | WO 2003005971 A2 * | 1/2003 |

OTHER PUBLICATIONS

Phaik-Eng Sum and Peter Petersen, Bioorganic & Medicinal Chemistry Letters, vol. 9, pp. 1459-1462, 1999.
Phaik-Eng Sum, et al., Abstract (1 page) and Poster (29 pages), 18th International Symposium on Medicinal Chemistry, Copenhagen, Denmark, Aug. 15-19, 2004.
Phaik-Eng Sum, et al.; J. Med. Chem.; vol. 37; No. 1; pp. 184-188; 1994.
International Search Report, Apr. 14, 2005.
Chopra, Handbook of Experimental Pharmacology, Springer-Verlag, vol. 78, pp. 317-392, 1985.
Richard C. Larock, Comprehensive Transformations, VCH Publishers, pp. 411-415; 1989.
S. B. Levy, et al.; Antimicrob; Agents Chemotherapy; vol. 33; pp. 1373-1374; 1989.
A.A. Salyers, et al.; Mol. Microbiol. vol. 4; pp. 151-156; 1990.

* cited by examiner

*Primary Examiner*—Joseph K. McKane
*Assistant Examiner*—Michael Barker
(74) *Attorney, Agent, or Firm*—Daniel B. Moran

(57) ABSTRACT

This invention provides compounds of the formula:

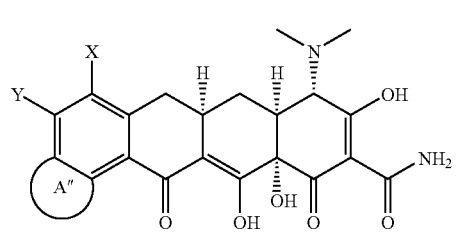

wherein A", X and Y are defined in the specification. These compounds are useful as antibacterial agents.

17 Claims, No Drawings

OXAZOLE DERIVATIVES OF TETRACYCLINES

This application claims priority from copending Provisional Application Nos. 60/527,928 filed Dec. 8, 2003 and 60/584,823 filed Jul. 1, 2004 the entire disclosures of which are hereby incorporated by reference.

FIELD OF THE INVENTION

The present invention relates to novel oxazole derivatives of tetracyclines which are useful as antibiotic agents and exhibit antibacterial activity against a wide spectrum of organisms including organisms which are resistant to tetracyclines and other antibiotics. This invention also relates to novel tetracycline intermediates useful for making the novel compounds and novel methods for producing the novel compounds and the intermediate compounds.

BACKGROUND OF THE INVENTION

Since 1947 a variety of tetracycline antibiotics have been synthesized and described for the treatment of infectious diseases in man and animals. Tetracyclines inhibit protein synthesis by binding to the 30S subunit of the bacterial ribosome preventing binding of aminoacyl RNA (Chopra, Handbook of Experimental Pharmacology, Vol. 78, 317–392, Springer-Verlag, 1985). Resistance to tetracyclines has emerged among many clinically important microorganisms which limit the utility of these antibiotics. There are two major mechanisms of bacterial resistance to tetracyclines: a) energy-dependent efflux of the antibiotic mediated by proteins located in the cytoplasmic membrane which prevents intracellular accumulation of tetracycline (S. B. Levy, et al., Antimicrob. Agents Chemotherapy 33, 1373–1374 (1989); and b) ribosomal protection mediated by a cytoplasmic protein which interacts with the ribosome such that tetracycline no longer binds or inhibits protein synthesis (A. A. Salyers, B. S. Speers and N. B. Shoemaker, Mol. Microbiol, 4:151–156, 1990). The efflux mechanism of resistance is encoded by resistance determinants designated tetA-tetL. They are common in many Gram-negative bacteria (resistance genes Class A–E), such as Enterobacteriaceae, *Pseudomonas, Haemophilus* and *Aeromonas*, and in Gram-positive bacteria (resistance genes Class K and L), such as *Staphylococcus, Bacillus* and *Streptococcus*. The ribosomal protection mechanism of resistance is encoded by resistance determinants designated TetM, N and O, and is common in *Staphylococcus, Streptococcus, Campylobacter, Gardnerella, Haemophilus* and *Mycoplasma* (A. A. Salyers, B. S. Speers and N. B. Shoemaker, Mol. Microbiol, 4:151–156 1990).

A particularly useful tetracycline compound is 7-(dimethylamino)-6-demethyl-6-deoxytetracycline, known as minocycline (see U.S. Pat. No. 3,148,212, U.S. Pat. No. RE 26,253 and U.S. Pat. No. 3,226,436 discussed below). However, strains harboring the tetB (efflux in gram-negative bacteria) mechanism, but not tetK (efflux in *Staphylococcus*) are resistant to minocycline. Also, strains carrying tetM (ribosomal protection) are resistant to minocycline. This invention describes the synthesis of novel tetracycline compounds which demonstrate significant in vitro and in vivo activity vs. tetracycline and minocycline susceptible strains and some tetracycline and minocycline resistant strains, that is, those harboring the tetM (ribosomal protection) resistance determinants.

Duggar, U.S. Pat. No. 2,482,055, discloses the preparation of Aureomycin.RTM. by fermentation which have antibacterial activity. Growich et al., U.S. Pat. No. 3,007,965, disclose improvements to the fermentation preparation. Beereboom et al., U.S. Pat. No. 3,043,875 discloses tetracycline derivatives Boothe et al., U.S. Pat. No. 3,148,212, reissued as U.S. Pat. No. RE 26,253, and Petisi et al., U.S. Pat. No. 3,226,436, discloses tetracycline derivatives which are useful for treating bacterial infections. Blackwood et al., U.S. Pat. No. 3,200,149 discloses tetracycline derivatives which possess microbiological activity. Petisi et al., U.S. Pat. No. 3,338,963 discloses tetracycline compounds which have broad-spectrum antibacterial activity. Bitha et al., U.S. Pat. No. 3,341,585 discloses tetracycline compounds which have broad-spectrum antibacterial activity. Shu, U.S. Pat. No. 3,360,557 discloses 9-hydroxytetracyclines which have been found to possess antibacterial activity. Zambrano, U.S. Pat. No. 3,360,561 discloses a process for preparing 9-nitrotetracyclines. Martell et al., U.S. Pat. No. 3,518,306 discloses tetracyclines which possess in vivo antibacterial activity.

In U.S. Pat. No. 5,021,407 a method of overcoming the resistance of tetracycline resistant bacteria is disclosed. The method involves utilizing a blocking agent compound in conjunction with a tetracycline type antibiotic. This patent does not disclose novel tetracycline compounds which themselves have activity against resistant organisms. Described in U.S. Pat. No. 5,494,903 are 7-substituted-9-substituted amino-6-demethyl-6-deoxytetracyclines which have broad spectrum antibacterial activity.

In summary, none of the above patents teach or suggest the novel compounds of this application. In addition, none of the above patents teach or suggest novel tetracycline compounds of the invention having activity against tetracycline and minocycline resistant strains as well as strains which are normally susceptible to tetracyclines.

SUMMARY OF THE INVENTION

In accordance with the present invention, there is provided compounds represented by Formula (I);

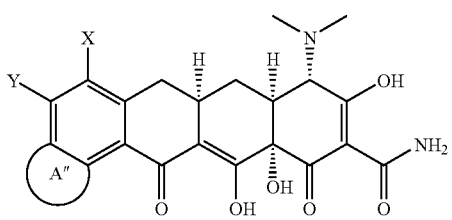

wherein:

X is selected from hydrogen, amino, $NR^{11}R^{12}$, alkyl of 1 to 12 carbon atoms optionally substituted, aryl of 6, 10 or 14 carbon atoms optionally substituted, vinyl optionally substituted, alkynyl of 2 to 12 carbon atoms optionally substituted and halogen;

A" is a moiety selected from the group:

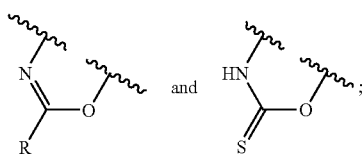

$R^{11}$ and $R^{12}$ are each independently H or alkyl of 1 to 12 carbon atoms or $R^{11}$ and $R^{12}$ when optionally taken together with the nitrogen atom to which each is attached form a 3 to 7 membered saturated hydrocarbon ring;

Y is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

R is selected from alkyl of 1 to 12 carbon atoms optionally substituted, alkenyl of 2 to 12 carbon atoms optionally substituted, alkynyl of 2 to 12 carbon atoms optionally substituted, —CH$_2$NR$^1$R$^2$, aryl of 6, 10 or 14 carbon atoms optionally substituted, aralkyl of 7 to 16 carbon atoms optionally substituted, aroyl of 7 to 13 carbon atoms optionally substituted, SR$^3$, heteroaryl of 5 or 6 ring atoms optionally substituted, containing 1 to 4 heteroatoms which may be the same or different, independently selected from nitrogen, oxygen and sulfur, and heteroarylcarbonyl of 5 or 6 ring atoms optionally substituted containing 1 to 4 heteroatoms which may be the same or different, independently selected from nitrogen, oxygen and sulfur;

R$^1$ and R$^2$ are each independently H or alkyl of 1 to 12 carbon atoms or R$^1$ and R$^2$ when optionally taken together with the nitrogen atom to which each is attached form a 3 to 7 membered saturated hydrocarbon ring;

R$^3$ is alkyl of 1 to 12 carbon atoms optionally substituted, —CH$_2$-aryl optionally substituted, aralkyl of 7 to 16 carbon atoms optionally substituted, aroyl, —CH$_2$(CO)OCH$_2$aryl optionally substituted, —CH$_2$-alkenyl of 2 to 12 carbon atoms optionally substituted, and —CH$_2$-alkynyl of 2 to 12 carbon atoms optionally substituted;

with the provisos that when X is NR$^{11}$R$^{12}$ and R$^{11}$ is hydrogen, then R$^{12}$ is methyl, ethyl, n-propyl, n-butyl, 1-methylethyl, 1-methylpropyl, 2-methylpropyl or 1,1-dimethylethyl; and that when R$^{11}$ is methyl or ethyl then R$^{12}$ is methyl, ethyl, n-propyl, 1-methylethyl, n-propyl, 1-methylpropyl, or 2-methylpropyl;

or a tautomer or pharmaceutically acceptable salts thereof.

Definitions

The term alkyl as a group or part of a group means a straight or branched alkyl moiety of 1 to 12 carbon atoms which can be optionally independently substituted with 1 to 3 substituents selected from the group halogen, amino, cyano, cycloalkyl of 3 to 6 carbon atoms, alkyl of 1 to 12 carbon atoms, aryl optionally substituted, phenyl, hydroxyl, alkoxy of 1 to 12 carbon atoms, NH-alkyl of 1 to 12 carbon atoms, N-cycloalkyl of 3 to 6 carbon atoms, NH-(alkyl of 1 to 12 carbon atoms)-aryl optionally substituted and heterocyclyl of 3 to 8 membered ring. In some embodiments of the invention alkyl is a moiety of 1 to 6 carbon atoms. In other embodiments of the invention alkyl is a moiety of 1 to 3 carbon atoms. In other embodiments alkyl is substituted by heterocyclyl of 4 to 7 ring members (e.g. pyrrolidinyl).

The term alkenyl means a straight or branched carbon chain of 2 to 12 carbon atoms having at least one site of unsaturation optionally independently substituted with 1 to 3 substituents selected from the group optionally substituted aryl, phenyl, heteroaryl, halogen, amino, cyano, alkyl of 1 to 12 carbon atoms, hydroxyl, and alkoxy of 1 to 12 carbon atoms.

The term vinyl means a moiety CH$_2$=CH—.

As used herein the term alkoxy as a group or part of a group refers to alkyl-O— wherein alkyl is hereinbefore defined.

As used herein the term aryl as a group or part of a group, e.g., aralkyl, aroyl, means an aromatic moiety having 6, 10 or 14 carbon atoms preferably 6 to 10 carbon atoms, which can be optionally substituted with 1 to 3 substituents independently selected from halogen, nitro, cyano, alkenyl, hydroxyl, alkyl, haloalkyl, alkoxy, benzyloxy, amino, alkylamino, dialkylamino, carboxyl, alkoxycarbonyl, methylenedioxy and phenyl. In particular, aryl is phenyl or naphthyl optionally substituted with 1 to 3 substituents. Substituted phenyl may optionally be the moiety

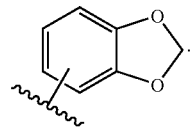

The term aralkyl as used herein of 7 to 16 carbon atoms means an alkyl substituted with an aryl group in which the aryl and alkyl group are previously defined. Non-limiting exemplary aralkyl groups include benzyl and phenethyl and the like.

Phenyl as used herein refers to a 6-membered carbon aromatic ring.

As used herein the term alkynyl includes both straight chain and branched moieties containing 2 to 12 carbon atoms having at least one carbon to carbon triple bond optionally substituted with 1 to 3 substituents independently selected from the group halogen, amino, cyano, alkyl of 1 to 12 carbon atoms, hydroxyl, and alkoxy of 1 to 12 carbon atoms.

As used herein the term halogen or halo means F, Cl, Br or I.

As used herein the term cycloalkyl means a saturated monocyclic ring having from 3 to 6 carbon atoms. Exemplary cycloalkyl rings include but are not limited to cyclopropyl, cyclobutyl, cyclopentyl, and cyclohexyl. In an embodiment of the invention cycloalkyl is a moiety of 5 or 6 carbon atoms.

As used herein, R$^1$ and R$^2$ and R$^{11}$ and R$^{12}$ when optionally taken together with the nitrogen atom to which each is attached form a 3 to 7 membered saturated hydrocarbon ring, where a non-limiting example is pyrrolidinyl,

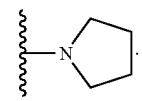

The term aroyl means an aryl-C(O)— group in which the aryl group is as previously defined. Non-limiting examples include benzoyl and naphthoyl.

The term heteroaryl means an aromatic heterocyclic, monocyclic ring of 5 or 6 ring atoms containing 1 to 4 heteroatoms independently selected from O, N and S. Heteroaryl rings may optionally be substituted with 1 to 3 substitutents selected from the group halogen, cyano, nitro, hydroxy, amino, alkylamino, dialkylamino, alkoxy, aryloxy, —CH$_2$OCOCH$_3$ and carboxy. Non-limiting heteroaryl moieties optionally substituted include: furanyl, thienyl, pyridyl, tetrazolyl, imidazo, thiazolyl and the like. Further included are benzofuranyl, benzothienyl and quinolinyl.

The term heteroarylcarbonyl means a heteroaryl-C(O)— group in which the heteroaryl group is as previously defined.

The term heterocyclyl as used herein represents a saturated 3 to 8 membered ring containing one to three heteroatoms selected from nitrogen, oxygen and sulfur. Representative examples are pyrrolidyl, piperidyl, piperazinyl, morpholinyl, thiomorpholinyl, aziridinyl, tetrahydrofuranyl and the like.

The term alkylheterocyclyl means an alkyl-heterocyclyl group in which the alkyl and heterocyclyl group are previously defined. Non-limiting exemplary alkylheterocyclyl groups include moieties of the formulae:

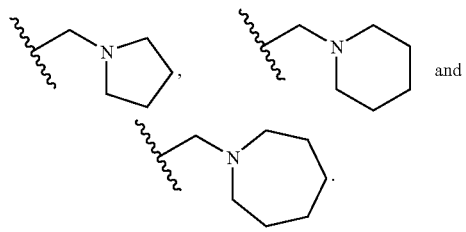

Some of the compounds of formula (I) may also exist in their tautomeric forms. Such forms although not explicitly indicated in the above formula are intended to be included within the scope of the present invention. For instance, compounds of formula (I) which exist as tautomers are depicted below:

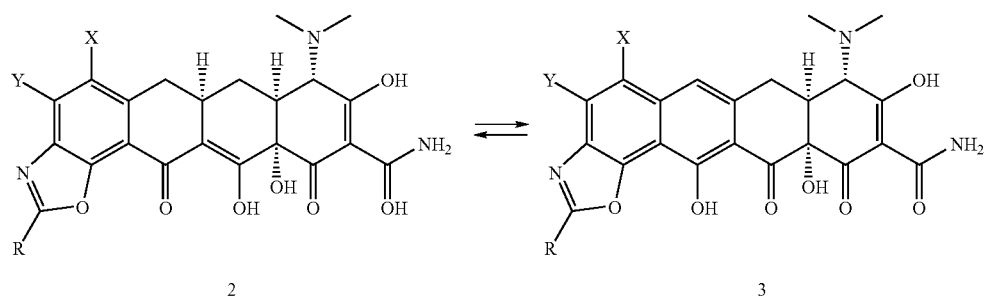

One embodiment of this invention is where R of Formula (I) is selected from the group alkyl of 1 to 6 carbon atoms, alkenyl of 2 to 6 carbon atoms, and alkyl-(heterocyclyl) selected from moieties of the group

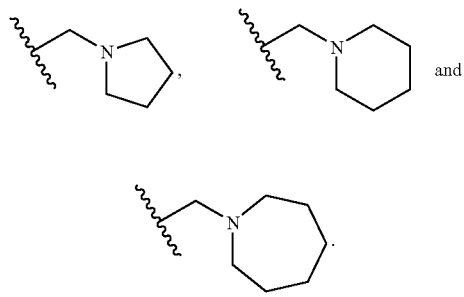

Another embodiment of the invention is where R of Formula (I) is phenyl optionally substituted with 1 to 3 substituents. In a preferred embodiment R is selected from moieties of the group

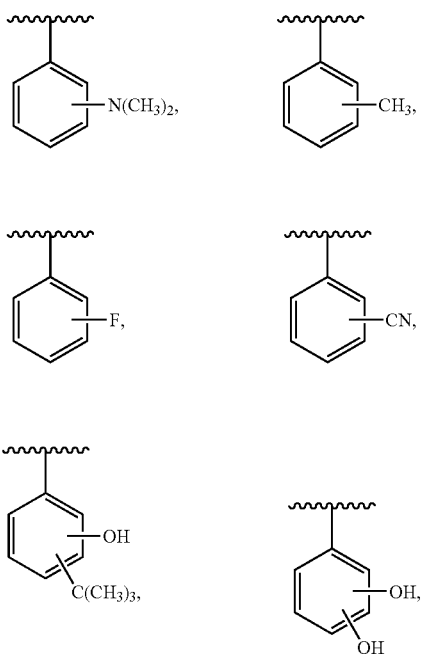

-continued

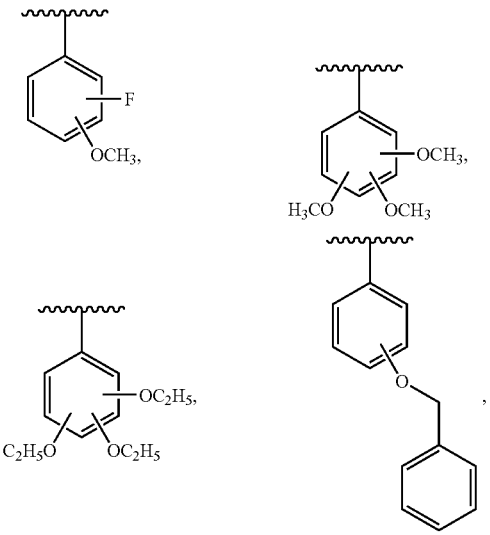

-continued

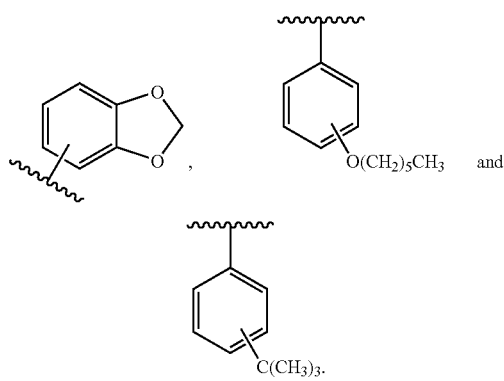

A further preferred embodiment of the invention is where R is heteroaryl. In a preferred embodiment R is selected from moieties of the group An additional embodiment of the invention is where R is alkyl of 1 to 6 carbon atoms optionally substituted, alkenyl of 2 to 6 carbon atoms optionally substituted,

NH(cycloalkyl of 5 to 6 carbon atoms),

NH(alkyl of 1 to 6 carbon atoms) and

NH(alkyl of 1 to 6 carbon atoms)-aryl optionally substituted.

In a preferred embodiment R is selected from moieties of the group

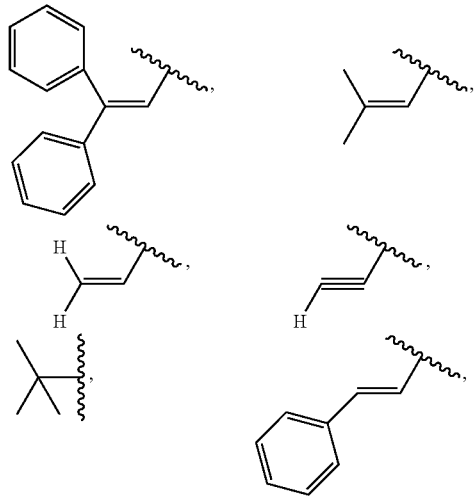

An additional embodiment of the invention is where R of Formula (I) is S-alkyl of 1 to 12 carbon atoms, S—CH$_2$-aryl optionally substituted and S—CH$_2$(CO)OCH$_2$aryl optionally substituted. In a preferred embodiment R is selected from moieties of the group

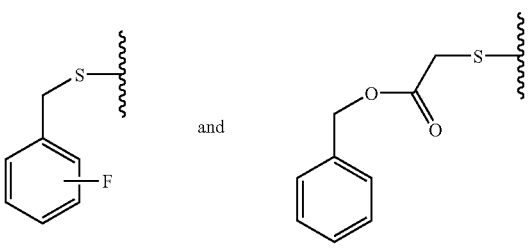

Preferred compounds of the invention include those selected from the group:

- (6aR,7aS,8S,11aS)-5,8-bis(dimethylamino)-2-(2,2-diphenylvinyl)-9,11a,12-trihydroxy-11,13-dioxo-6,6a,7,7a,8,11,11a,13-octahydrotetraceno[2,1-d][1,3]oxazole-10-carboxamide,
- (7aS,8S,11aS)-8-(dimethylamino)-9,11a,13-trihydroxy-2-(2-methyl-1-propenyl)-11,12-dioxo-7,7a,8,11,11a,12-hexahydronaphthaceno[2,1-d][1,3]oxazole-10-carboxamide,
- (6aR,7aS,8S,11aS)-2-tert-butyl-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-2-[(E)-2-(2-furyl)ethenyl]-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-11,13-dioxo-2-[(E)-2-phenylethenyl]-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-2-[(E)-2-(4-methoxyphenyl)ethenyl]-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-2-[(E)-2-(3-methoxyphenyl)ethenyl]-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-2-[(E)-2-(2-methoxyphenyl)ethenyl]-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-2-[(E)-2-(4-fluorophenyl)ethenyl]-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-2-[(E)-2-(2-fluorophenyl)ethenyl]-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-2-(chloromethyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-2-[(dimethylamino)methyl]-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-11,13-dioxo-2-(pyrrolidin-1-ylmethyl)-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-11,13-dioxo-2-[(propylamino)methyl]-6,6a,7,7a,8,11,11a,13-octahydrotetraceno[2,1-d][1,3]oxazole-10-carboxamide,
- (6aR,7aS,8S,11aS)-2-[(butylamino)methyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-11,13-dioxo-2-[(propylamino)methyl]-6,6a,7,7a,8,11,11a,13-octahydrotetraceno[2,1-d][1,3]oxazole-10-carboxamide and
- (6aR,7aS,8S,11aS)-2-[(tert-butylamino)methyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide.

Preferred compounds of the invention include those selected from the group:

- (7aS,8S,11aS)-8-(dimethylamino)-2-[4-(dimethylamino)phenyl]-9,11a,13-trihydroxy-11,12-dioxo-7,7a,8,11,11a,12-hexahydronaphthaceno[2,1-d][1,3]oxazole-10-carboxamide,
- (6aR,7aS,8S,11aS)-2-tert-butyl-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-2-(4-methylphenyl)-11,13-dioxo-6,6a,7,7a,8,11,11a,13-octahydrotetraceno[2,1-d][1,3]oxazole-10-carboxamide,
- (7aS,8S,11aS)-5,8-bis(dimethylamino)-2-(3-fluorophenyl)-9,11a,13-trihydroxy-11,12-dioxo-7,7a,8,11,11a,12-hexahydrotetraceno[2,1-d][1,3]oxazole-10-carboxamide,
- (6aR,7aS,8S,11aS)-2-(4-cyanophenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-2-[4-(dimethylamino)phenyl]-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-2-(5-tert-butyl-2-hydroxyphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-2-[4-(benzyloxy)phenyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-2-(2,4-dihydroxyphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-2-(3-fluoro-4-methoxyphenyl)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-2-(1,3-benzodioxol-5-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-11,13-dioxo-2-(2,4,6-trimethoxyphenyl)-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-11,13-dioxo-2-(2,4,5-triethoxyphenyl)-6,6a,7,7a,8,11,11a,13-octahydrotetraceno[2,1-d][1,3]oxazole-10-carboxamide,
- (6aR,7aS,8S,11aS)-5,8-bis(dimethylamino)-9,11a,12-trihydroxy-2-(1-methyl-1H-indol-2-yl)-11,13-dioxo-6,6a,7,7a,8,11,11a,13-octahydrotetraceno[2,1-d][1,3]oxazole-10-carboxamide,
- (6aR,7aS,8S,11aS)-2-(4-tert-butylphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide and (6aR,7aS,8S,11aS)-5,8-bis(dimethylamino)-2-[4-(hexyloxy)phenyl]-9,11a,12-trihydroxy-11,13-dioxo-6,6a,7,7a,8,11,11a,13-octahydrotetraceno[2,1-d][1,3]oxazole-10-carboxamide.

Preferred compounds include those selected from the group:
(6aR,7aS,8S,11aS)-5,8-bis(dimethylamino)-9,11a,12-trihydroxy-11,13-dioxo-2-thien-3-yl-6,6a,7,7a,8,11,11a,13-octahydrotetraceno[2,1-d][1,3]oxazole-10-carboxamide,
(6aR,7aS,8S,11aS)-2-(1-benzofuran-2-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
(6aR,7aS,8S,11aS)-5,8-bis(dimethylamino)-2-(2-furyl)-9,11a,12-trihydroxy-11,13-dioxo-6,6a,7,7a,8,11,11a,13-octahydrotetraceno[2,1-d][1,3]oxazole-10-carboxamide,
{5-[(6aR,7aS,8S,11aS)-10-(aminocarbonyl)-5,8-bis(dimethylamino)-9,11a,12-trihydroxy-11,13-dioxo-6,6a,7,7a,8,11,11a,13-octahydrotetraceno[2,1-d][1,3]oxazol-2-yl]-2-furyl}methyl acetate,
(6aR,7aS,8S,11aS)-2-(1-benzothien-3-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide,
(6aR,7aS,8S,11aS)-5,8-bis(dimethylamino)-9,11a,12-trihydroxy-11,13-dioxo-2-(1,3-thiazol-2-yl)-6,6a,7,7a,8,11,11a,13-octahydrotetraceno[2,1-d][1,3]oxazole-10-carboxamide,
(6aR,7aS,8S,11aS)-5,8-bis(dimethylamino)-9,11a,12-trihydroxy-11,13-dioxo-2-pyridin-4-yl-6,6a,7,7a,8,11,11a,13-octahydrotetraceno[2,1-d][1,3]oxazole-10-carboxamide and
(6aR,7aS,8S,11aS)-5,8-bis(dimethylamino)-9,11a,12-trihydroxy-11,13-dioxo-2-pyridin-3-yl-6,6a,7,7a,8,11,11a,13-octahydrotetraceno[2,1-d][1,3]oxazole-10-carboxamide.

An additional embodiment of the invention is a process for the preparation of a compound of the formula

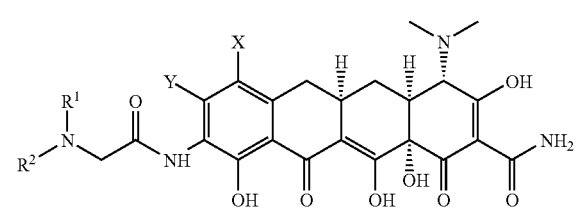

or a pharmaceutically acceptable salt thereof
wherein:
X is selected from hydrogen, amino, $NR^{11}R^{12}$, alkyl of 1 to 12 carbon atoms optionally substituted, aryl of 6, 10 or 14 carbon atoms optionally substituted, vinyl optionally substituted, alkynyl of 2 to 12 carbon atoms optionally substituted and halogen;
$R^1$ and $R^2$ are each independently H or alkyl of 1 to 12 carbon atoms or $R^1$ and $R^2$ when optionally taken together with the nitrogen atom to which each is attached form a 3 to 7 membered saturated hydrocarbon ring;
$R^{11}$ and $R^{12}$ are each independently H or alkyl of 1 to 12 carbon atoms or $R^{11}$ and $R^{12}$ when optionally taken together with the nitrogen atom to which each is attached form a 3 to 7 membered saturated hydrocarbon ring;
Y is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

comprising the steps:
a. reacting 7-(substituted)-8-(substituted)-9-amino-6-demethyl-6-deoxytetracycline of the formula

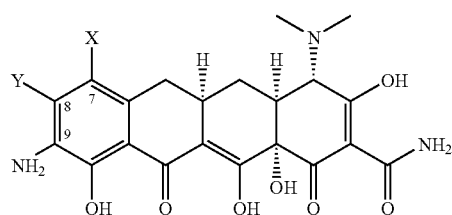

or a pharmaceutically acceptable salt thereof with 2-chlorotrimethoxyethane in an aprotic solvent to afford a chloro compound of the formula

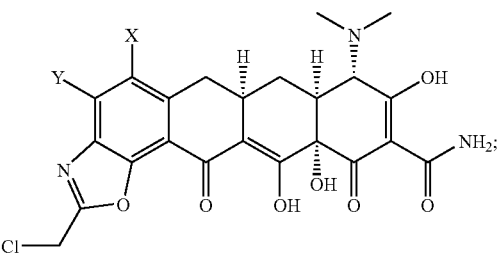

b. reacting the chloro compound with an amine $R^1R^2NH$ to form a substituted amine of the formula

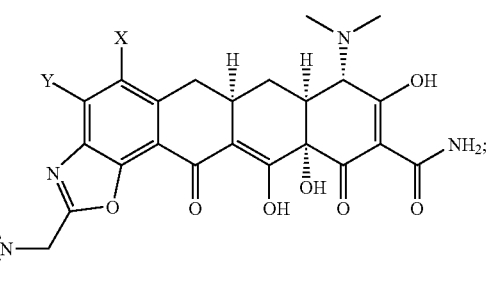

c. hydrolyzing the substituted amine with acid to give a compound of the formula

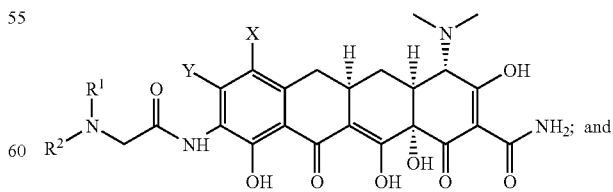

d. isolating the compound or a pharmaceutically acceptable salt thereof.

In a preferred embodiment of the process X is $N(CH_3)_2$ and the amine $R^1R^2NH$ is t-butyl amine.

In a preferred embodiment of the process the compound [4S-(4α,4aα,5aα,12aα)]-4,7-Bis(dimethylamino)-9-[2-(1,1-dimethylethylamino)acetylamino]-1,4,4a,5,5a,6,11,12a-octahydro-3,10,12,12a-tetrahydroxy-1,11-dioxo-2-naphthacenecarboxamide or a pharmaceutically acceptable salt thereof is prepared.

A further embodiment of the invention is a process for the preparation of a compound of the formula

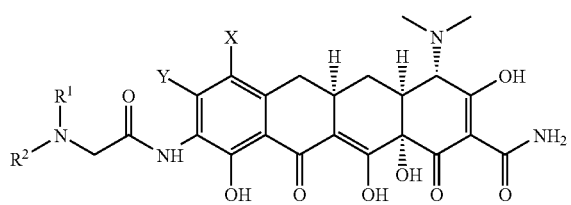

wherein:
X is selected from hydrogen, amino, $NR^{11}R^{12}$, alkyl of 1 to 12 carbon atoms optionally substituted, aryl of 6, 10 or 14 carbon atoms optionally substituted, vinyl, optionally substituted, alkynyl of 2 to 12 carbon atoms optionally substituted and halogen;
$R^1$ and $R^2$ are each independently H or alkyl of 1 to 12 carbon atoms or $R^1$ and $R^2$ when optionally taken together with the nitrogen atom to which each is attached form a 3 to 7 membered saturated hydrocarbon ring;
$R^{11}$ and $R^{12}$ are each independently H or alkyl of 1 to 12 carbon atoms or $R^{11}$ and $R^{12}$ when optionally taken together with the nitrogen atom to which each is attached form a 3 to 7 membered saturated hydrocarbon ring;
Y is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

or a pharmaceutically acceptable salt thereof comprising the steps:
a. reacting 7-(substituted)-8-(substituted)-9-amino-6-demethyl-6-deoxytetracycline of the formula

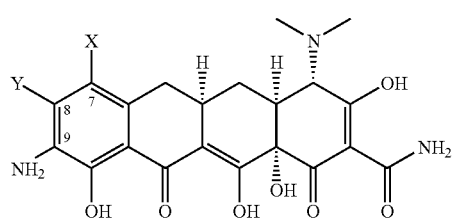

or a pharmaceutically acceptable salt thereof with 2-chlorotrimethoxyethane in an aprotic solvent to afford a chloro compound of the formula

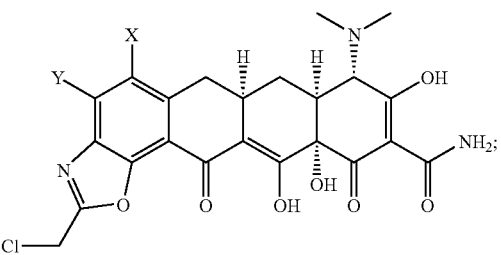

b. reacting the chloro compound with acid to give 9-(2-chloromethylcarbonylamino)substituted-6-demethyl-6-deoxytetracycline of the formula

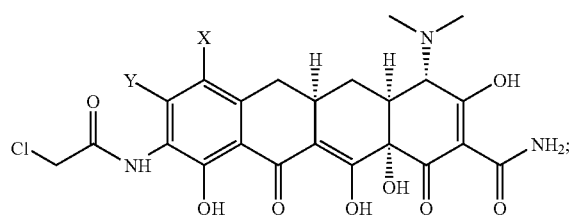

c. reacting the 9-(2-chloromethylcarbonylamino)substituted-6-demethyl-6-deoxytetracycline with amine $R^1R^2NH$ to give a compound of the formula

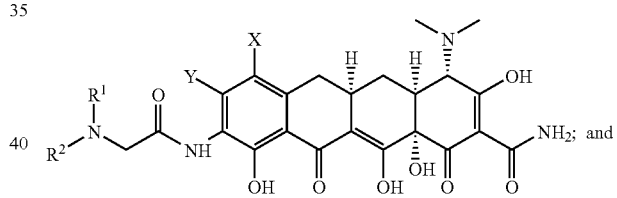

d. isolating the compound or a pharmaceutically acceptable salt thereof.

In a preferred embodiment of the process X is $N(CH_3)_2$ and the amine $R^1R^2NH$ is t-butyl amine.

In a preferred embodiment of the process the compound [4S-(4α,4aα,5aα,12aα)]-4,7-Bis(dimethylamino)-9-[2-(1,1-dimethylethylamino)acetylamino]-1,4,4a,5,5a,6,11,12a-octahydro-3,10,12,12a-tetrahydroxy-1,11-dioxo-2-naphthacenecarboxamide or a pharmaceutically acceptable salt thereof is prepared.

An additional embodiment of the invention is a compound of the formula

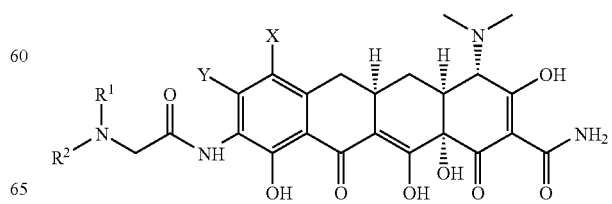

or a pharmaceutically acceptable salt thereof wherein:

X is selected from hydrogen, amino, $NR^{11}R^{12}$, alkyl of 1 to 12 carbon atoms optionally substituted, aryl of 6, 10 or 14 carbon atoms optionally substituted, vinyl optionally substituted, alkynyl of 2 to 12 carbon atoms optionally substituted and halogen;

$R^1$ and $R^2$ are each independently H or alkyl of 1 to 12 carbon atoms or $R^1$ and $R^2$ when optionally taken together with the nitrogen atom to which each is attached form a 3 to 7 membered saturated hydrocarbon ring;

$R^{11}$ and $R^{12}$ are each independently H or alkyl of 1 to 12 carbon atoms or $R^{11}$ and $R^{12}$ when optionally taken together with the nitrogen atom to which each is attached form a 3 to 7 membered saturated hydrocarbon ring;

Y is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

produced by the process comprising the steps:

a. reacting 7-(substituted)-8-(substituted)-9-amino-6-demethyl-6-deoxytetracycline of the formula

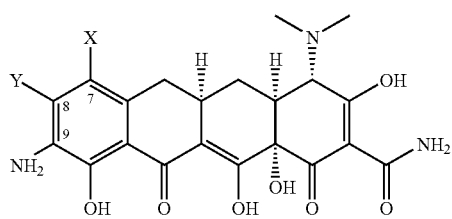

or a pharmaceutically acceptable salt thereof with 2-chlorotrimethoxyethane in an aprotic solvent to afford a chloro compound of the formula

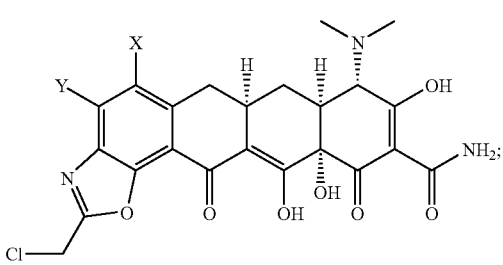

b. reacting the chloro compound with an amine $R^1R^2NH$ to form a substituted amine of the formula

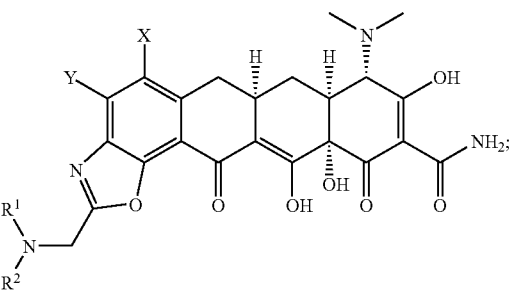

c. hydrolyzing the substituted amine with acid to give a compound of the formula

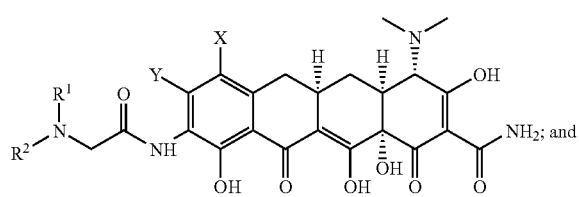

d. isolating the compound or a pharmaceutically acceptable salt thereof.

In a preferred embodiment of the process X is $N(CH_3)_2$ and the amine $R^1R^2NH$ is t-butyl amine.

In a preferred embodiment of the process the compound [4S-(4α,4aα,5aα,12aα)]-4,7-Bis(dimethylamino)-9-[2-(1,1-dimethylethylamino)acetylamino]-1,4,4a,5,5a,6,11,12a-octahydro-3,10,12,12a-tetrahydroxy-1,11-dioxo-2-naphthacenecarboxamide or a pharmaceutically acceptable salt thereof is prepared.

In an additional embodiment of the invention a compound of the formula

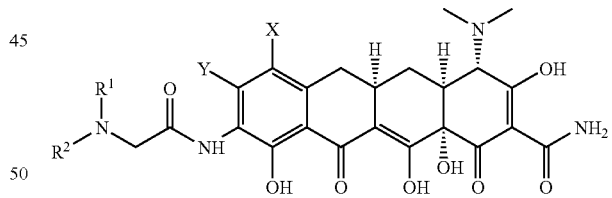

wherein:

X is selected from hydrogen, amino, $NR^{11}R^{12}$, alkyl of 1 to 12 carbon atoms optionally substituted, aryl of 6, 10 or 14 carbon atoms optionally substituted, vinyl optionally substituted, alkynyl of 2 to 12 carbon atoms optionally substituted and halogen;

$R^1$ and $R^2$ are each independently H or alkyl of 1 to 12 carbon atoms or when optionally taken together with the nitrogen atom to which each is attached form a 3 to 7 membered saturated hydrocarbon ring;

$R^{11}$ and $R^{12}$ are each independently H or alkyl of 1 to 12 carbon atoms or $R^{11}$ and $R^{12}$ when optionally taken together with the nitrogen atom to which each is attached form a 3 to 7 membered saturated hydrocarbon ring;

Y is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

or a pharmaceutically acceptable salt thereof produced by the process comprising the steps:

a. reacting 7-(substituted)-8-(substituted)-9-amino-6-demethyl-6-deoxytetracycline of the formula

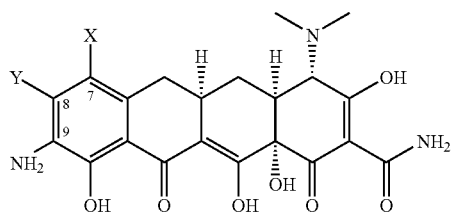

or a pharmaceutically acceptable salt thereof with 2-chlorotrimethoxyethane in an aprotic solvent to afford a chloro compound of the formula

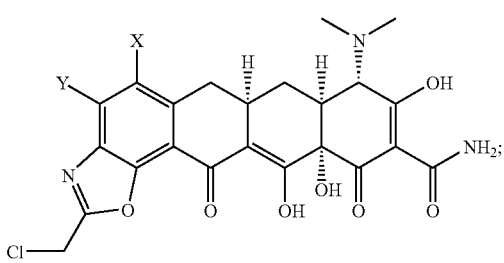

b. reacting the chloro compound with acid to give 9-(2-chloromethylcarbonylamino)substituted-6-demethyl-6-deoxytetracycline of the formula

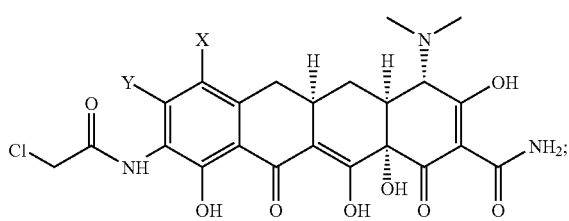

c. reacting the 9-(2-chloromethylcarbonylamino)substituted-6-demethyl-6-deoxytetracycline with amine $R^1R^2NH$ to give a compound of the formula

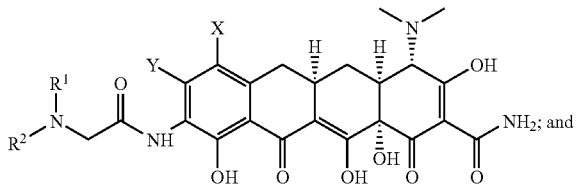

d. isolating the compound or a pharmaceutically acceptable salt thereof.

In a preferred embodiment of the process X is $N(CH_3)_2$ and the amine $R^1R^2NH$ is t-butyl amine.

In a preferred embodiment the compound [4S-(4α,4aα,5aα,12aα)]-4,7-Bis(dimethylamino)-9-[2-(1,1-dimethylethylamino)acetylamino]-1,4,4a,5,5a,6,11,12a-octahydro-3,10,12,12a-tetrahydroxy-1,11-dioxo-2-naphthacenecarboxamide or a pharmaceutically acceptable salt thereof is prepared by the process.

DESCRIPTION OF THE PREFERRED EMBODIMENTS

The novel compounds of the present invention may be readily prepared in accordance with the following Scheme I.

The starting 7-(substituted)-8-(substituted)-9-amino-6-demethyl-6-deoxytetracyclines 1 or pharmaceutically acceptable salts thereof where X and Y are hereinbefore defined are reacted with aldehyde RCHO in the presence of 2,3-dichloro-5,6-dicyano-1,4-benzoquinone (DDQ) to afford benzoxazole 2 and 3 (Procedure A). As further described, reaction of 7-(substituted)-8-(substituted)-9-amino-6-demethyl-6-deoxytetracyclines 1 or pharmaceutically acceptable salts thereof where X and Y are hereinbefore defined are reacted with 2-chloro-1,1,1-trimethoxyethane in an aprotic solvent such as N,N-dimethylformamide (DMF) to give chloromethylbenzoxazole 4, optionally isolated, then converted to substituted amine 5 by further reaction with an amine 9 (Procedure B). Hydrolysis of amine 5 affords 9-(2-substituted aminomethyl carbonylamino)substituted-6-dimethyl-6-deoxytetracycline 6 (Procedure D). Hydrolysis of chloromethylbenzoxazole 4 gives 9-(2-chloromethylcarbonylamino)substituted-6-demethyl-6-deoxytetracycline 7 which may be further reacted with amine 9 to give 9-(2-substituted aminomethyl carbonylamino)substituted-6-dimethyl-6-deoxytetracycline 6.

Additionally, reaction of 7-(substituted)-8-(substituted)-9-amino-6-demethyl-6-deoxytetracyclines 1 or pharmaceutically acceptable salts thereof with thiocarbonyldiimidazole provides thio 8 followed by alkylation with $RCH_2Br$ in the presence of an amine which includes N,N-diisopropylethylamine affords oxazole 10 (Procedure C).

Preferably, amine 9 in the preparation of 9-(2-substituted aminomethyl carbonylamino)substituted-6-dimethyl-6-deoxytetracycline 6, in Scheme I is t-butylamine.

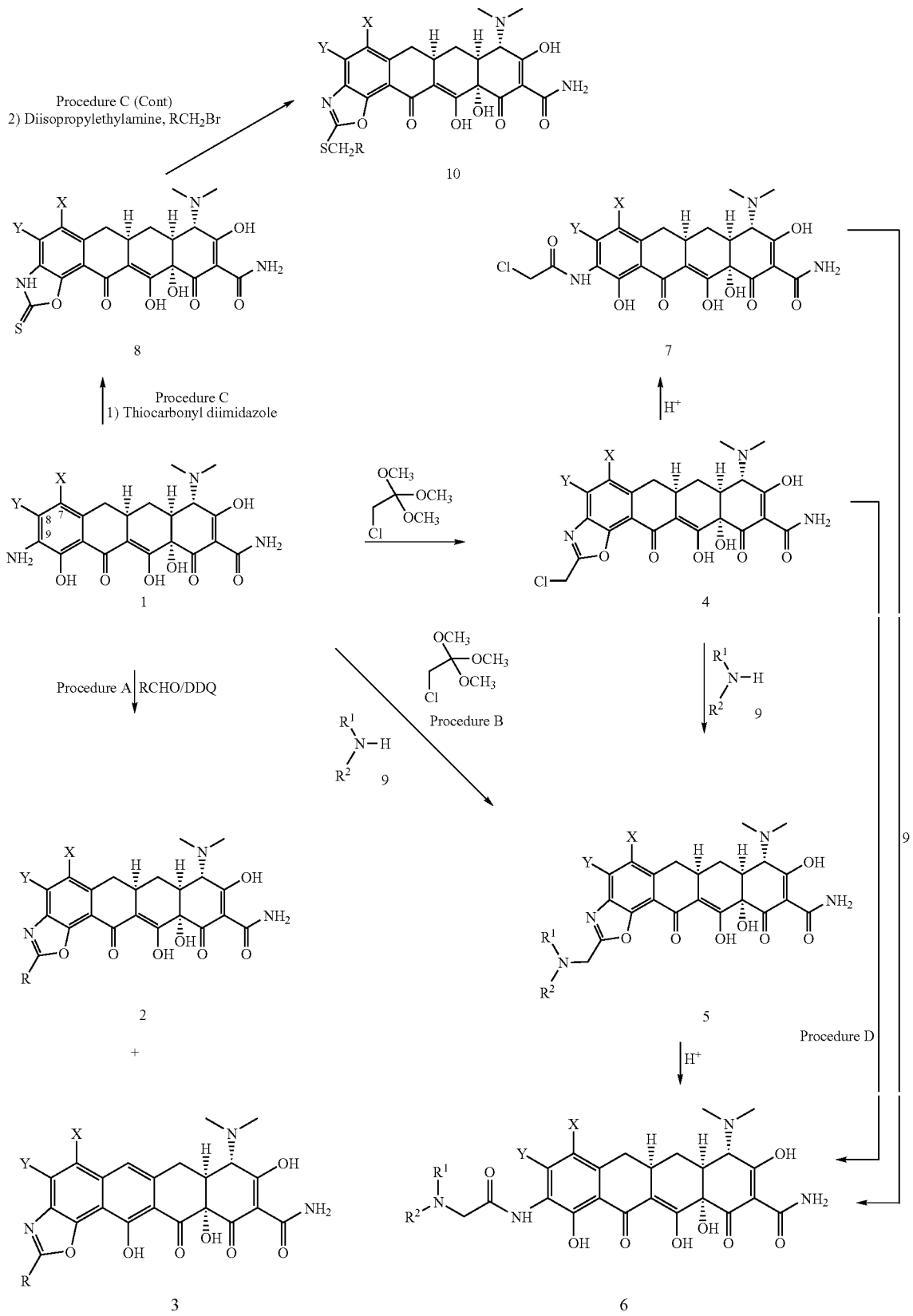

As shown in Scheme II, the starting 7-(substituted)-8-(substituted)-9-amino-6-demethyl-6-deoxytetracyclines 1 or pharmaceutically acceptable salts thereof where X and Y are hereinbefore defined are reacted with a methyl orthoester to afford methyl benzoxazole derivative 11. Acid hydrolysis of methyl benzoxazole derivative 11 affords N-acetyl derivative 12.

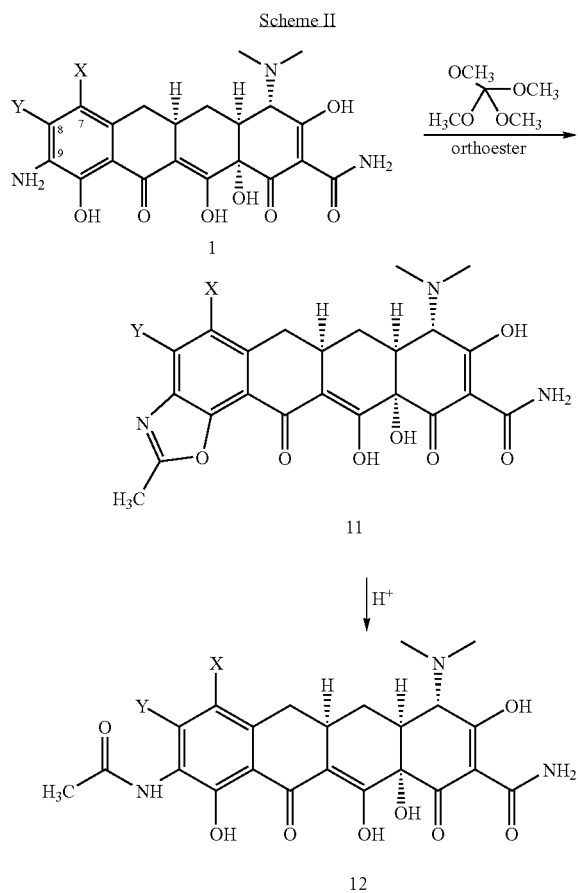

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have center of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

Pharmaceutically acceptable salts of the compounds of the invention may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411–415, 1989). Preferably, the compounds of the invention are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate alkylsulfonate or arylsulfonate. The salt formation preferentially occurs with the C(4)-dimethylamino group when forming inorganic salts. The salts are preferred for oral and parenteral administration.

Standard Pharmacological Test Procedures

Methods for in Vitro Antibacterial Evaluation

The Minimum Inhibitory Concentration (MIC)

Antimicrobial susceptibility testing. The in vitro activities of the antibiotics are determined by the broth microdilution method as recommended by the National Committee for Clinical Laboratory Standards (NCCLS) (1). Mueller-Hinton II broth (MHBII) (BBL Cockeysville, Md.) is the medium employed in the testing procedures. Microtiter plates containing serial dilutions of each antimicrobial agent are inoculated with each organism to yield the appropriate density ($10^5$ CFU/ml) in a 100 µl final volume. The plates are incubated for 18–22 hours at 35° C. in ambient air. The minimal inhibitory concentration for all isolates is defined as the lowest concentration of antimicrobial agent that completely inhibits the growth of the organism as detected by the unaided eye.

1. NCCLS. 2000. Methods for Dilution Antimicrobial Susceptibility Tests for Bacteria That Grow Aerobically; Approved Standards: M7-A5, vol. 20. National Committe for Clinical Laboratory Standards, Wayne, Pa.

TABLE I

ANTIBACTERIAL ACTIVITY OF
(7-SUBSTITUTED)-8-(SUBSTITUTED)-9-(SUBSTITUTED)-TETRACYCLINES
MIC (µg/ml) COMPOUND

|  | Example 1 | Example 2 | Example 3 | Example 4 | Example 5 | Example 6 |
|---|---|---|---|---|---|---|
| 1 E. coli GC2270 (tet(M)) | >64 | >64 | >64 | >64 | >64 | >64 |
| 2 E. coli GC4559 (parent GC4560) | >64 | >64 | >64 | >64 | >64 | >64 |
| 3 E. coli GC4560 (IMP mutant) | 32 | 8 | 16 | 16 | 4 | 8 |
| 4 E. coli GC2203 (ATCC Control) | >64 | >64 | >64 | >64 | >64 | >64 |
| 5 E. coli GC1073 (tet(B)) | >64 | >64 | >64 | >64 | >64 | >64 |
| 6 S. aureus GC1131 (Clinical) | 16 | 8 | 2 | 16 | 4 | 4 |

TABLE I-continued

ANTIBACTERIAL ACTIVITY OF (7-SUBSTITUTED)-8-(SUBSTITUTED)-9-(SUBSTITUTED)-TETRACYCLINES MIC (µg/ml) COMPOUND

|  | Example 1 | Example 2 | Example 3 | Example 4 | Example 5 | Example 6 |
|---|---|---|---|---|---|---|
| 7 S. aureus GC6466 (tet(M)) | 32 | 8 | 2 | 32 | 4 | 4 |
| 8 S. aureus GC6467 (tet(M) + (K)) | 32 | 8 | 2 | 32 | 4 | 4 |
| 9 S. aureus GC1079 (tet(K)) | 16 | 8 | 1 | 16 | 4 | 4 |
| 10 S. aureus GC4536 (Smith MP - In Vivo) | 16 | 8 | 2 | 32 | 4 | 4 |
| 11 S. aureus GC2216 (ATCC Control) | 16 | 8 | 2 | 32 | 4 | 4 |
| 12 E. faecalis GC4555 (ATCC Control) | 32 | 8 | 2 | 32 | 4 | 8 |
| 13 E. faecalis GC2267 (tet(L) + (M) + (S)) | 32 | 8 | 2 | 32 | 4 | 4 |
| 14 E. faecalis GC2242 (Van-resistant) | 16 | 8 | 2 | 32 | 4 | 4 |
| 15 S. pneumoniae* GC4465 (Clinical) | 16 | 8 | 2 | 16 | 16 | 16 |
| 16 S. pneumoniae* GC1894 (Clinical) | 8 |  |  | 32 | 8 | 16 |
| 17 S. pyogenes* GC4563 (Clinical) | 8 | 8 | 8 | 16 | 16 | 16 |
| 18 M. catarrhalis* GC6907 (Clinical) | >64 |  |  | 16 | 16 | 32 |
| 19 H. influenzae <> GC6896 (ATCC Control) | >64 |  |  | >64 | >64 | >64 |
| 20 C. albicans GC3066 ATCC (Control) | >64 | >64 | >64 | >64 | >64 | >64 |

TABLE II

ANTIBACTERIAL ACTIVITY OF (7-SUBSTITUTED)-8-(SUBSTITUTED)-9-SUBSTITUTED)-TETRACYCLINES MIC (µg/ml) COMPOUND

|  | Example 7 | Example 8 | Example 10 | Example 11 |
|---|---|---|---|---|
| 1 E. coli GC2270 (tet(M)) | >64 | >64 | >64 | >64 |
| 2 E. coli GC4559 (parent GC4560) | >64 | >64 | >64 | >64 |
| 3 E. coli GC4560 (IMP mutant) | 8 | 16 | 32 | >64 |
| 4 E. coli GC2203 (ATCC Control) | >64 | >64 | >64 | >64 |
| 5 E. coli GC1073 (tet(B)) | >64 | >64 | >64 | >64 |
| 6 S. aureus GC1131 (Clinical) | 8 | 8 | 8 | 32 |
| 7 S. aureus GC6466 (tet(M)) | 8 | 16 | 16 | 64 |
| 8 S. aureus GC6467 (tet(M) + (K)) | 8 | 8 | 16 | 32 |
| 9 S. aureus GC1079 (tet(K)) | 8 | 16 | 16 | 64 |
| 10 S. aureus GC4536 (Smith MP - In Vivo) | 8 | 16 | 16 | 64 |
| 11 S. aureus GC2216 (ATCC Control) | 8 | 8 | 16 | 64 |
| 12 E. faecalis GC4555 (ATCC Control) | 8 | 32 | 16 | 64 |
| 13 E. faecalis GC2267 (tet(L) + (M) + (S)) | 8 | 16 | 16 | >64 |
| 14 E. faecalis GC2242 (Van-resistant) | 8 | 8 | 8 | 64 |
| 15 S. pneumoniae* GC4465 (Clinical) | 8 | 32 | 16 | 32 |
| 16 S. pneumoniae* GC1894 (Clinical) | 16 | 16 | 8 | 32 |
| 17 S. pyogenes* GC4563 (Clinical) | 8 | 16 | 16 | 32 |
| 18 M. catarrhalis* GC6907 (Clinical) | 4 | 64 | >64 | 32 |
| 19 H. influenzae <> GC6896 (ATCC Control) | 64 | >64 | >64 | >64 |
| 20 C. albicans GC3066 ATCC (Control) | >64 | >64 | >64 | >64 |

TABLE III

ANTIBACTERIAL ACTIVITY OF (7-SUBSTITUTED)-8-(SUBSTITUTED)-9-(SUBSTITUTED)-TETRACYCLINES MIC (µg/ml) COMPOUND

|  | Example 12 | Example 13 | Example 14 | Example 15 | Example 16 |
|---|---|---|---|---|---|
| 1 E. coli GC2270 (tet(M)) | >64 | >64 | >64 | >64 | >64 |
| 2 E. coli GC4559 (parent GC4560) | >64 | >64 | >64 | >64 | >64 |
| 3 E. coli GC4560 (IMP mutant) | 4 | 4 | 16 | 32 | 16 |
| 4 E. coli GC2203 (ATCC Control) | 32 | >64 | >64 | >64 | >64 |
| 5 E. coli GC1073 (tet(B)) | >64 | >64 | >64 | >64 | >64 |
| 6 S. aureus GC1131 (Clinical) | 4 | 4 | 4 | 64 | 16 |
| 7 S. aureus GC6466 (tet(M)) | 8 | 4 | 4 | 64 | 16 |
| 8 S. aureus GC6467 (tet(M) + (K)) | 8 | 8 | 8 | 64 | 16 |
| 9 S. aureus GC1079 (tet(K)) | 8 | 4 | 4 | 64 | 16 |
| 10 S. aureus GC4536 (Smith MP - In Vivo) | 8 | 8 | 4 | 64 | 16 |
| 11 S. aureus GC2216 (ATCC Control) | 4 | 4 | 4 | 64 | 16 |
| 12 E. faecalis GC4555 (ATCC Control) | 8 | 8 | 8 | 64 | 16 |
| 13 E. faecalis GC2267 (tet(L) + (M) + (S)) | 8 | 8 | 8 | 64 | 16 |
| 14 E. faecalis GC2242 (Van-resistant) | 8 | 8 | 4 | 64 | 16 |
| 15 S. pneumoniae* GC4465 (Clinical) | 8 | 32 | 16 | >64 | >64 |
| 16 S. pneumoniae* GC1894 (Clinical) | 8 | 16 | 16 | >64 | >64 |

TABLE III-continued

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 12 | Example 13 | Example 14 | Example 15 | Example 16 |
|---|---|---|---|---|---|
| 17 S. pyogenes* GC4563 (Clinical) | 4 | 16 | 16 | >64 | 64 |
| 18 M. catarrhalis* GC6907 (Clinical) | 4 | 16 | 4 | 64 | >64 |
| 19 H. influenzae <> GC6896 (ATCC Control) | 16 | >64 | >64 | >64 | >64 |
| 20 C. albicans GC3066 ATCC (Control) | >64 | >64 | >64 | >64 | >64 |

TABLE IV

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 17 | Example 18 | Example 19 | Example 20 | Example 21 |
|---|---|---|---|---|---|
| 1 E. coli GC2270 (tet(M)) | >64 | >64 | >64 | >64 | >64 |
| 2 E. coli GC4559 (parent GC4560) | >64 | >64 | >64 | >64 | >64 |
| 3 E. coli GC4560 (IMP mutant) | 4 | 4 | 4 | 32 | >64 |
| 4 E. coli GC2203 (ATCC Control) | >64 | >64 | >64 | >64 | >64 |
| 5 E. coli GC1073 (tet(B)) | >64 | >64 | >64 | >64 | >64 |
| 6 S. aureus GC1131 (Clinical) | 8 | 4 | 4 | 32 | 64 |
| 7 S. aureus GC6466 (tet(M)) | 8 | 4 | 4 | 32 | 32 |
| 8 S. aureus GC6467 (tet(M) + (K)) | 8 | 4 | 4 | 32 | 32 |
| 9 S. aureus GC1079 (tet(K)) | 8 | 4 | 4 | 32 | 32 |
| 10 S. aureus GC4536 (Smith MP - In Vivo) | 8 | 4 | 8 | 64 | 64 |
| 11 S. aureus GC2216 (ATCC Control) | 8 | 4 | 4 | 32 | 32 |
| 12 E. faecalis GC4555 (ATCC Control) | 8 | 4 | 8 | 64 | >64 |
| 13 E. faecalis GC2267 (tet(L) + (M) + (S)) | 16 | 4 | 8 | 64 | 64 |
| 14 E. faecalis GC2242 (Van-resistant) | 8 | 4 | 4 | 32 | 32 |
| 15 S. pneumoniae* GC4465 (Clinical) | 32 | 16 | 4 | >64 | >64 |
| 16 S. pneumoniae* GC1894 (Clinical) | 32 | 16 | 4 | 64 | >64 |
| 17 S. pyogenes* GC4563 (Clinical) | 16 | 16 | 8 | 32 | >64 |
| 18 M. catarrhalis* GC6907 (Clinical) | 16 | 8 | 16 | 32 | >64 |
| 19 H. influenzae <> GC6896 (ATCC Control) | >64 | >64 | >64 | >64 | >64 |
| 20 C. albicans GC3066 ATCC (Control) | >64 | >64 | >64 | >64 | >64 |

TABLE V

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 22 | Example 24 | Example 25 | Example 26 |
|---|---|---|---|---|
| 1 E. coli GC2270 (tet(M)) | >64 | >64 | >64 | >64 |
| 2 E. coli GC4559 (parent GC4560) | >64 | >64 | >64 | >64 |
| 3 E. coli GC4560 (IMP mutant) | 8 | 32 | 8 | 32 |
| 4 E. coli GC2203 (ATCC Control) | >64 | >64 | >64 | >64 |
| 5 E. coli GC1073 (tet(B)) | >64 | >64 | >64 | >64 |
| 6 S. aureus GC1131 (Clinical) | 8 | 32 | 8 | 16 |
| 7 S. aureus GC6466 (tet(M)) | 8 | 32 | 4 | 16 |
| 8 S. aureus GC6467 (tet(M) + (K)) | 8 | 32 | 8 | 16 |
| 9 S. aureus GC1079 (tet(K)) | 8 | 32 | 4 | 32 |
| 10 S. aureus GC4536 (Smith MP - In Vivo) | 8 | 32 | 8 | 32 |
| 11 S. aureus GC2216 (ATCC Control) | 8 | 64 | 4 | 16 |
| 12 E. faecalis GC4555 (ATCC Control) | 8 | 32 | 8 | 32 |
| 13 E. faecalis GC2267 (tet(L) + (M) + (S)) | 8 | 32 | 4 | 16 |
| 14 E. faecalis GC2242 (Van-resistant) | 8 | 32 | 4 | 16 |
| 15 S. pneumoniae* GC4465 (Clinical) | 32 | 64 | 32 | >64 |
| 16 S. pneumoniae* GC1894 (Clinical) | 32 | 64 | 32 | >64 |
| 17 S. pyogenes* GC4563 (Clinical) | 16 | 32 | 16 | 64 |
| 18 M. catarrhalis* GC6907 (Clinical) | 16 | >64 | 16 | >64 |
| 19 H. influenzae <> GC6896 (ATCC Control) | >64 | >64 | >64 | >64 |
| 20 C. albicans GC3066 ATCC (Control) | >64 | >64 | >64 | >64 |

TABLE VI

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 27 | Example 28 | Example 29 | Example 30 | Example 31 |
|---|---|---|---|---|---|
| 1 E. coli GC2270 (tet(M)) | >64 | >64 | >64 | >64 | >64 |
| 2 E. coli GC4559 (parent GC4560) | >64 | >64 | >64 | >64 | >64 |
| 3 E. coli GC4560 (IMP mutant) | 32 | 16 | 8 | 8 | 4 |
| 4 E. coli GC2203 (ATCC Control) | >64 | >64 | >64 | >64 | >64 |
| 5 E. coli GC1073 (tet(B)) | >64 | >64 | >64 | >64 | >64 |
| 6 S. aureus GC1131 (Clinical) | 8 | 8 | 8 | 4 | 8 |
| 7 S. aureus GC6466 (tet(M)) | 16 | 8 | 8 | 8 | 4 |
| 8 S. aureus GC6467 (tet(M) + (K)) | 8 | 8 | 8 | 8 | 8 |
| 9 S. aureus GC1079 (tet(K)) | 8 | 16 | 8 | 8 | 8 |
| 10 S. aureus GC4536 (Smith MP - In Vivo) | 16 | 16 | 8 | 8 | 8 |
| 11 S. aureus GC2216 (ATCC Control) | 8 | 8 | 8 | 4 | 8 |
| 12 E. faecalis GC4555 (ATCC Control) | 16 | 16 | 8 | 8 | 8 |
| 13 E. faecalis GC2267 (tet(L) + (M) + (S)) | 8 | 8 | 8 | 4 | 8 |
| 14 E. faecalis GC2242 (Van-resistant) | 8 | 8 | 8 | 4 | 8 |
| 15 S. pneumoniae* GC4465 (Clinical) | 64 | 32 | 32 | 16 | 8 |
| 16 S. pneumoniae* GC1894 (Clinical) | 64 | 64 | 32 | 16 | 8 |
| 17 S. pyogenes* GC4563 (Clinical) | 64 | 16 | 16 | 16 | 8 |
| 18 M. catarrhalis* GC6907 (Clinical) | >64 | 64 | 16 | 32 | 16 |
| 19 H. influenzae <> GC6896 (ATCC Control) | >64 | >64 | >64 | >64 | >64 |
| 20 C. albicans GC3066 ATCC (Control) | >64 | >64 | >64 | >64 | >64 |

TABLE VII

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 32 | Example 33 | Example 34 | Example 35 | Example 36 |
|---|---|---|---|---|---|
| 1 E. coli GC2270 (tet(M)) | >64 | >64 | >64 | 16 | 4 |
| 2 E. coli GC4559 (parent GC4560) | >64 | >64 | >64 | 8 | 4 |
| 3 E. coli GC4560 (IMP mutant) | >64 | 16 | 32 | 0.50 | 1 |
| 4 E. coli GC2203 (ATCC Control) | >64 | 64 | >64 | 4 | 2 |
| 5 E. coli GC1073 (tet(B)) | >64 | >64 | >64 | 32 | 4 |
| 6 S. aureus GC1131 (Clinical) | >64 | 16 | 32 | 0.50 | 4 |
| 7 S. aureus GC6466 (tet(M)) | >64 | 32 | 64 | 1 | 4 |
| 8 S. aureus GC6467 (tet(M) + (K)) | >64 | 32 | 64 | 8 | 16 |
| 9 S. aureus GC1079 (tet(K)) | >64 | 16 | 32 | 4 | 4 |
| 10 S. aureus GC4536 (Smith MP - In Vivo) | >64 | 16 | 64 | 1 | 4 |
| 11 S. aureus GC2216 (ATCC Control) | >64 | 16 | 32 | 0.50 | 2 |
| 12 E. faecalis GC4555 (ATCC Control) | 64 | 16 | 32 | 1 | 4 |
| 13 E. faecalis GC2267 (tet(L) + (M) + (S)) | >64 | 16 | 32 | 4 | 4 |
| 14 E. faecalis GC2242 (Van-resistant) | 64 | 16 | 32 | 1 | 4 |
| 15 S. pneumoniae* GC4465 (Clinical) | 16 | 16 | 32 | 0.50 | 1 |
| 16 S. pneumoniae* GC1894 (Clinical) | 8 | 32 | 64 | 0.25 | 1 |
| 17 S. pyogenes* GC4563 (Clinical) | 16 | 8 | 32 | 0.25 | 1 |
| 18 M. catarrhalis* GC6907 (Clinical) | 32 | 8 | 16 | 0.50 | 1 |
| 19 H. influenzae <> GC6896 (ATCC Control) | >64 | 32 | >64 | 2 | 4 |
| 20 C. albicans GC3066 ATCC (Control) | >64 | >64 | >64 | >64 | >64 |

TABLE VIII

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 37 | Example 38 | Example 39 |
|---|---|---|---|
| 1 E. coli GC2270 (tet(M)) | 4 | 32 | 32 |
| 2 E. coli GC4559 (parent GC4560) | 2 | 32 | 32 |
| 3 E. coli GC4560 (IMP mutant) | 1 | 8 | 8 |
| 4 E. coli GC2203 (ATCC Control) | 2 | 32 | 32 |
| 5 E. coli GC1073 (tet(B)) | 2 | 32 | 32 |
| 6 S. aureus GC1131 (Clinical) | 4 | 32 | 32 |
| 7 S. aureus GC6466 (tet(M)) | 4 | 32 | 32 |
| 8 S. aureus GC6467 (tet(M) + (K)) | 8 | >64 | >64 |
| 9 S. aureus GC1079 (tet(K)) | 4 | 64 | 64 |
| 10 S. aureus GC4536 (Smith MP - In Vivo) | 4 | 16 | 32 |

TABLE VIII-continued

ANTIBACTERIAL ACTIVITY OF
(7-SUBSTITUTED)-8-(SUBSTITUTED)-9-(SUBSTITUTED)-TETRACYCLINES
MIC (μg/ml) COMPOUND

|  | Example 37 | Example 38 | Example 39 |
|---|---|---|---|
| 11 S. aureus GC2216 (ATCC Control) | 4 | 32 | 32 |
| 12 E. faecalis GC4555 (ATCC Control) | 2 | 16 | 32 |
| 13 E. faecalis GC2267 (tet(L) + (M) + (S)) | 4 | 64 | 64 |
| 14 E. faecalis GC2242 (Van-resistant) | 2 | 16 | 32 |
| 15 S. pneumoniae* GC4465 (Clinical) | 1 | 4 | 8 |
| 16 S. pneumoniae* GC1894 (Clinical) | 1 | 4 | 8 |
| 17 S. pyogenes* GC4563 (Clinical) | 1 | 4 | 8 |
| 18 M. catarrhalis* GC6907 (Clinical) | 1 | 4 | 8 |
| 19 H. influenzae <> GC6896 (ATCC Control) | 4 | 64 | 64 |
| 20 C. albicans GC3066 ATCC (Control) | >64 | >64 | >64 |

When the compounds of the invention are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from about 2.0 mg/kg of body weight to about 100.0 mg/kg of body weight may be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions of compounds of the invention from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not to be construed as limiting the scope of the invention.

Example of Procedure A

EXAMPLE 1

(6aR,7aS,8S,11aS)-5,8-bis(dimethylamino)-2-(2,2-diphenylvinyl)-9,11a,12-trihydroxy-11,13-dioxo-6,6a,7,7a,8,11,11a,13-octahydrotetraceno[2,1-d][1,3]oxazole-10-carboxamide

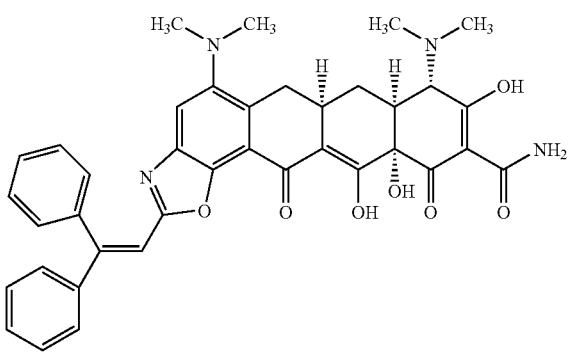

9-aminominocycline sulfate salt (0.500 g, 0.748 mmol) is dissolved in anhydrous DMF and treated with β-phenylcinnamaldehyde (0.779 g, 3.74 mmol, 5 equivalents) The solution is then treated with DDQ (0.085 g, 0.374 mmol, 0.5 equivalents) and stirred at room temperature for 5 min. ES+ mass spectrometry showed a 1:1 ratio of product and starting material. A second portion of DDQ (0.068 g, 0.300 mmol, 0.4 equivalents) is added. After approximately 5 minutes, acetonitrile (7.5 mL) is added, and the entire reaction mixture is poured slowly into ether (750 mL.) The pink solid is removed by filtration and washed with fresh ether to yield 0.480 g of the crude product. This material is dissolved in water (75 mL) to give a solution at pH 2.2, which is extracted with dichloromethane (2×100 mL.) The pH of the aqueous layer is raised to 3.0 with aqueous ammonia, and the solution is again extracted with dichloromethane (2×100 mL.) The four organic extracts are dried ($Na_2SO_4$), filtered and concentrated to a volume of about 2 mL. A small portion of methanol (1 mL) is added, and the concentrated solution is treated dropwise with 1M HCl in ether. The solid precipitate is filtered, washed with fresh ether and dried under vacuum the product as its HCl salt.

Selected 1H NMR signals: δ 4.26 (s, 1H), 7.13 (s, 1H), 7.26–7.45 (m, 8H), 7.63 (s, 1H), 9.08 (s, 1H), 9.54 (s, 1H).

The compounds of this invention listed below in Examples 2 to 37 are prepared substantially following the method described in detail hereinabove in Example 1 using procedure A.

EXAMPLE 2

(7aS,8S,11aS)-8-(dimethylamino)-9,11a,13-trihydroxy-2-(2-methyl-1-propenyl)-11,12-dioxo-7,7a,8,11,11a,12-hexahydronaphthaceno[2,1-d][1,3]oxazole-10-carboxamide

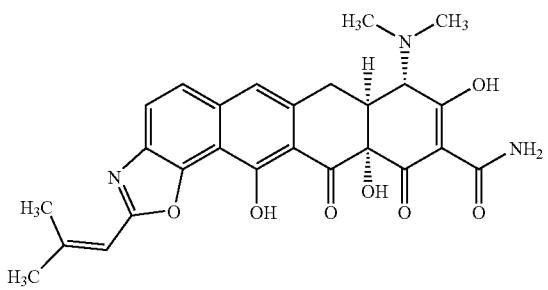

MS m/z 492 (M+H) HRMS: calcd for $C_{26}H_{26}N_3O_7$: 491.16925. found: (ESI+), 492.1765.

EXAMPLE 3

(7aS,8S,11aS)-8-(dimethylamino)-2-[4-(dimethylamino)phenyl]-9,11a,13-trihydroxy-11,12-dioxo-7,7a,8,11,11a,12-hexahydronaphthaceno[2,1-d][1,3]oxazole-10-carboxamide

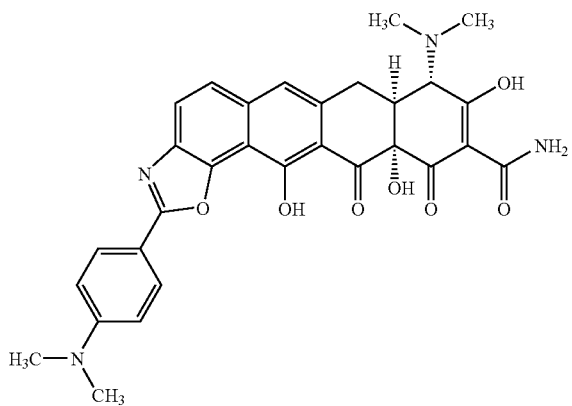

HRMS: calcd for $C_{30}H_{29}N_3O_7$: 566.1958. found: (ESI+), 557.2030.

EXAMPLE 4

(6aR,7aS,8S,11aS)-2-tert-butyl-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

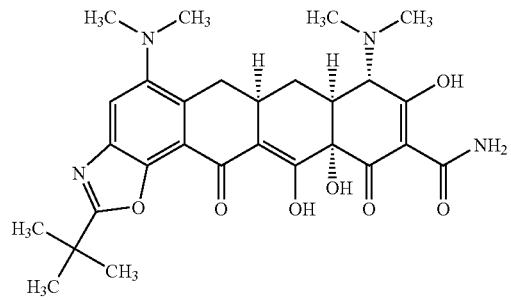

MS (ESI) m/z 539.3 (M+H); MS (ESI) m/z 270.4 (M+2H); HRMS: calcd for $C_{28}H_{34}N_4O_7$.HCl: 574.2194. found: (ESI–), 537.23462.

EXAMPLE 5

(6aR,7aS,8S,11aS)-5,8-bis(dimethylamino)-9,11a,12-trihydroxy-2-(4-methylphenyl)-11,13-dioxo-6,6a,7,7a,8,11,11a,13-octahydrotetraceno[2,1-d][1,3]oxazole-10-carboxamide

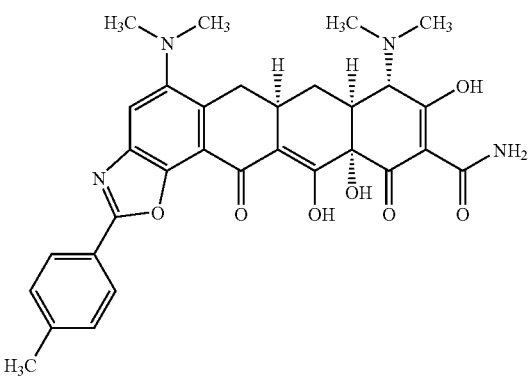

MS (ESI) m/z 573.3 (M+H); MS (ESI) m/z 287 (M+2H); HRMS: calcd for $C_{31}H_{32}N_4O_7$.HCl: 608.2038. found: (ESI–), 571.21905.

EXAMPLE 6

(7aS,8S,11aS)-5,8-bis(dimethylamino)-2-(3-fluorophenyl)-9,11a,13-trihydroxy-11,12-dioxo-7,7a,8,11,11a,12-hexahydrotetraceno[2,1-d][1,3]oxazole-10-carboxamide

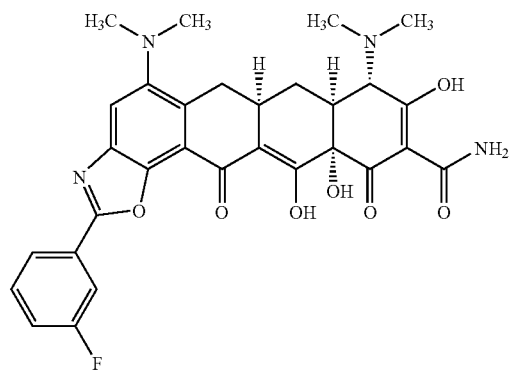

EXAMPLE 7

(6aR,7aS,8S,11aS)-2-(4-cyanophenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

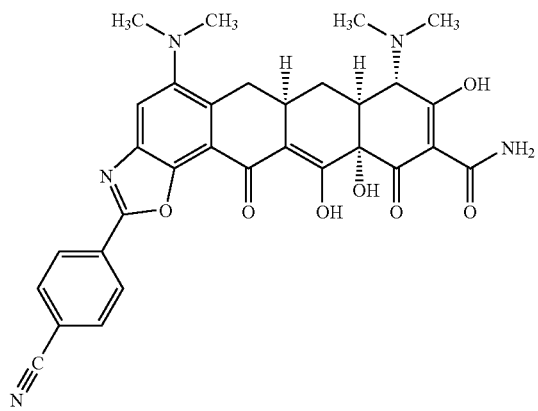

MS (ESI) m/z 584.4 (M+H); HRMS: calcd for $C_{31}H_{29}N_5O_7$·HCl: 619.1834. found: (ESI−), 582.19817.

EXAMPLE 8

(6aR,7aS,8S,11aS)-5,8-bis(dimethylamino)-2-[4-(dimethylamino)phenyl]-9,11a,12-trihydroxy-11,13-dioxo-6,6a,7,7a,8,11,11a,13-octahydrotetraceno[2,1-d][1,3]oxazole-10-carboxamide

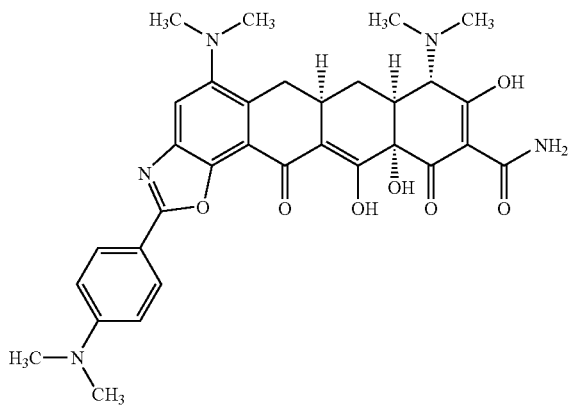

MS (ESI) m/z 602.2 (M+H); MS (ESI) m/z 301.8 (M+2H); HRMS: calcd for $C_{32}H_{35}N_5O_7$·HCl: 637.2303. found: (ESI−), 600.24521.

EXAMPLE 9

(6aR,7aS,8S,11aS)-5,8-bis(dimethylamino)-2-(2,2-diphenylvinyl)-9,11a,12-trihydroxy-11,13-dioxo-6,6a,7,7a,8,11,11a,13-octahydrotetraceno[2,1-d][1,3]oxazole-10-carboxamide

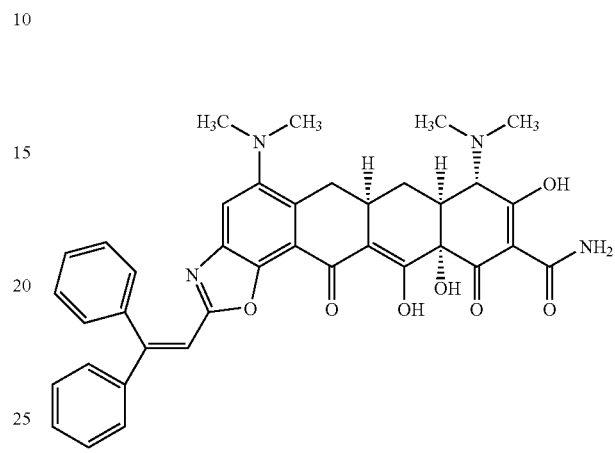

MS (ESI) m/z 661.3 (M+H); MS (ESI) m/z 331.3 (M+2H); HRMS: calcd for $C_{38}H_{36}N_4O_7$·HCl: 696.2351. found: (ESI−), 659.24957.

EXAMPLE 10

(6aR,7aS,8S,11aS)-2-(5-tert-butyl-2-hydroxyphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

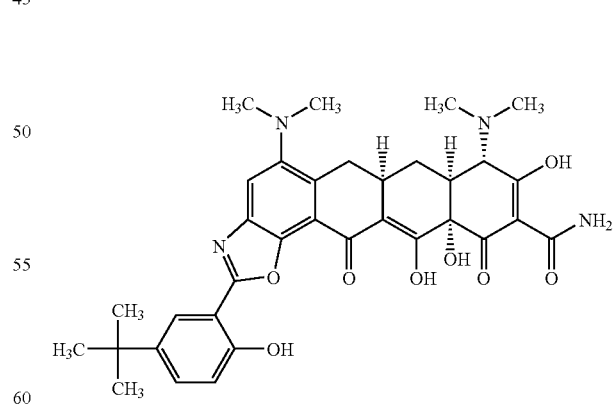

MS (ESI) m/z 631.4 (M+H); HRMS: calcd for $C_{34}H_{38}N_4O_8$·HCl: 666.2456. found: (ESI+), 631.27753.

EXAMPLE 11

(6aR,7aS,8S,11aS)-2-[4-(benzyloxy)phenyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

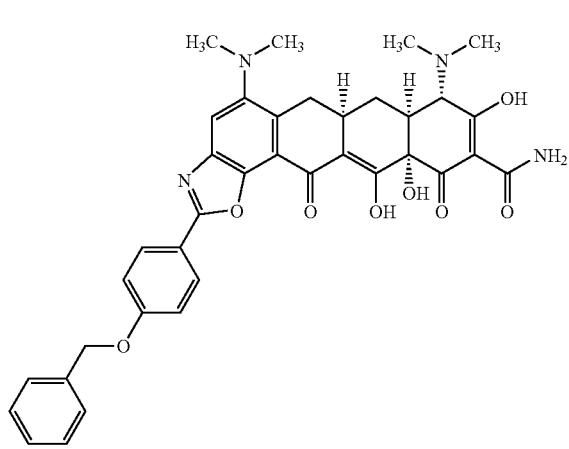

MS (ESI) m/z 665.2 (M+H); HRMS: calcd for $C_{37}H_{36}N_4O_8 \cdot HCl$: 700.2300. found: (ESI+), 665.26096.

EXAMPLE 12

(6aR,7aS,8S,11aS)-2-(2,4-dihydroxyphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

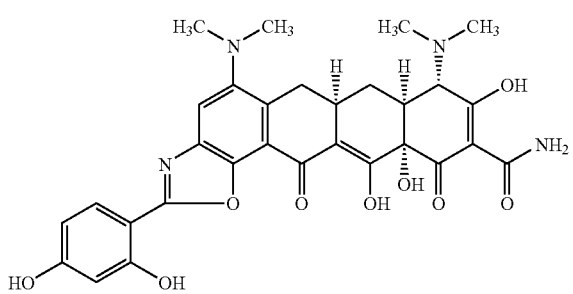

MS (ESI) m/z 591.2 (M+H); HRMS: calcd for $C_{30}H_{30}N_4O_9 \cdot HCl$: 626.1780. found: (ESI−), 589.1927.

EXAMPLE 13

(6aR,7aS,8S,11aS)-5,8-bis(dimethylamino)-2-(3-fluoro-4-methoxyphenyl)-9,11a,12-trihydroxy-11,13-dioxo-6,6a,7,7a,8,11,11a,13-octahydrotetraceno[2,1-d][1,3]oxazole-10-carboxamide

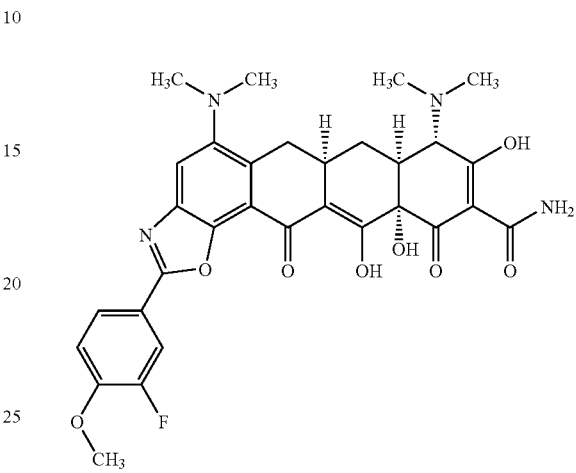

MS (ESI) m/z 607.3 (M+H); MS (ESI) m/z 304 (M+2H); HRMS: calcd for $C_{31}H_{31}FN_4O_8 \cdot HCl$: 642.1893. found: (ESI−), 605.20519.

EXAMPLE 14

(6aR,7aS,8S,11aS)-2-(1,3-benzodioxol-5-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

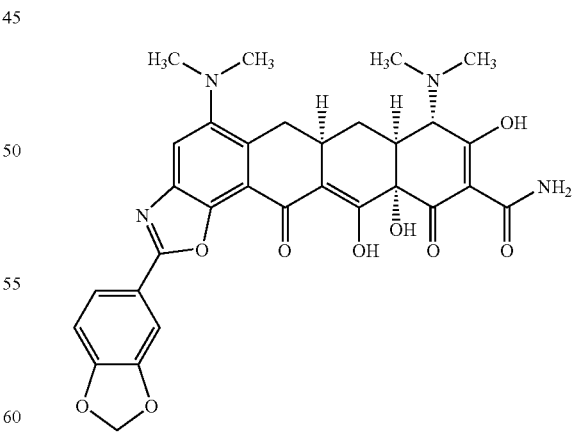

MS (ESI) m/z 603.3 (M+H); MS (ESI) m/z 302.1 (M+2H); HRMS: calcd for $C_{31}H_{30}N_4O_9 \cdot HCl$: 638.1780. found: (ESI+), 603.20953.

EXAMPLE 15

(6aR,7aS,8S,11aS)-5,8-bis(dimethylamino)-9,11a,12-trihydroxy-11,13-dioxo-2-(2,4,6-trimethoxyphenyl)-6,6a,7,7a,8,11,11a,13-octahydrotetraceno[2,1-d][1,3]oxazole-10-carboxamide

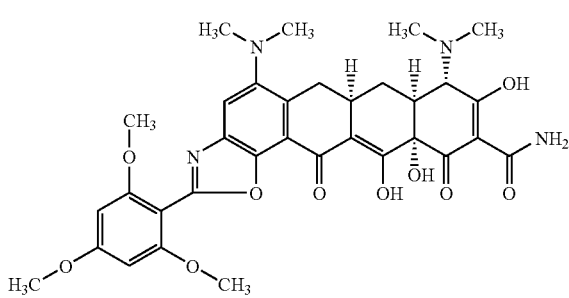

MS (ESI) m/z 649.2 (M+H); HRMS: calcd for $C_{33}H_{36}N_4O_{10}$·HCl: 684.2198. found: (ESI−), 647.23441.

EXAMPLE 16

(6aR,7aS,8S,11aS)-5,8-bis(dimethylamino)-9,11a,12-trihydroxy-11,13-dioxo-2-(2,4,5-triethoxyphenyl)-6,6a,7,7a,8,11,11a,13-octahydrotetraceno[2,1-d][1,3]oxazole-10-carboxamide

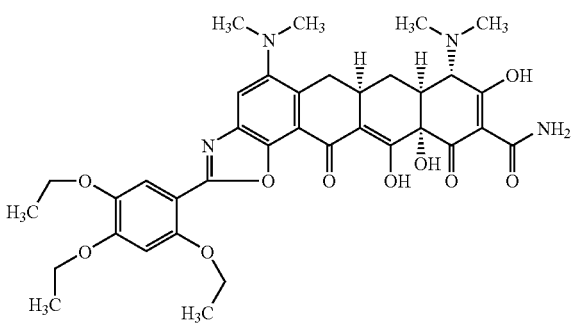

MS (ESI) m/z 691.3 (M+H); HRMS: calcd for $C_{36}H_{42}N_4O_{10}$·HCl: 726.2668. found: (ESI+), 691.29817.

EXAMPLE 17

(6aR,7aS,8S,11aS)-5,8-bis(dimethylamino)-9,11a,12-trihydroxy-11,13-dioxo-2-thien-3-yl-6,6a,7,7a,8,11,11a,13-octahydrotetraceno[2,1-d][1,3]oxazole-10-carboxamide

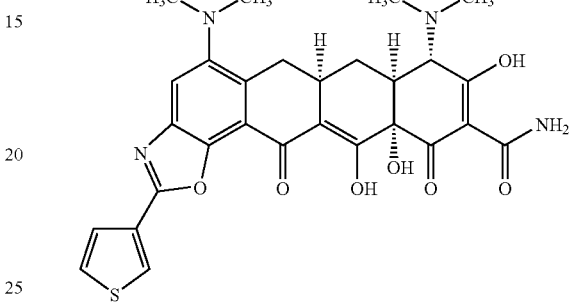

MS (ESI) m/z 565.2 (M+H); MS (ESI) m/z 283.4 (M+2H); HRMS: calcd for $C_{28}H_{28}N_4O_7S$·HCl: 600.1445. found: (ESI−), 563.15992.

EXAMPLE 18

(6aR,7aS,8S,11aS)-2-(1-benzofuran-2-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

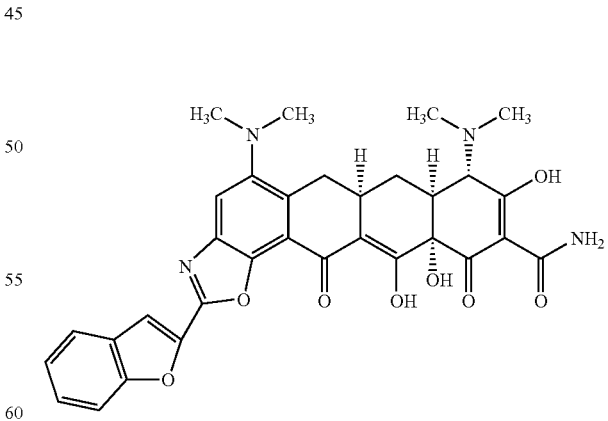

MS (ESI) m/z 599.3 (M+H); HRMS: calcd for $C_{32}H_{30}N_4O_8$·HCl: 634.1830. found: (ESI−), 597.19811.

EXAMPLE 19

(6aR,7aS,8S,11aS)-5,8-bis(dimethylamino)-9,11a,12-trihydroxy-2-(1-methyl-1H-indol-2-yl)-11,13-dioxo-6,6a,7,7a,8,11,11a,13-octahydrotetraceno[2,1-d][1,3]oxazole-10-carboxamide

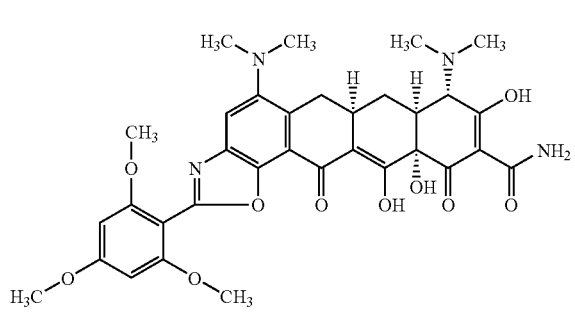

MS (ESI) m/z 612.2 (M+H); HRMS: calcd for C$_{33}$H$_{33}$N$_5$O$_7$.HCl: 647.2147. found: (ESI+), 612.24406.

EXAMPLE 20

(6aR,7aS,8S,11aS)-5,8-bis(dimethylamino)-2-(2-furyl)-9,11a,12-trihydroxy-11,13-dioxo-6,6a,7,7a,8,11,11a,13-octahydrotetraceno[2,1-d][1,3]oxazole-10-carboxamide

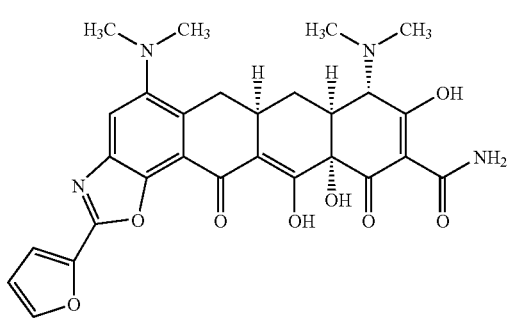

MS (ESI) m/z 549.3 (M+H); HRMS: calcd for C$_{28}$H$_{28}$N$_4$O$_8$.HCl: 584.1674. found: (ESI–), 547.1822.

EXAMPLE 21

{5-[(6aR,7aS,8S,11aS)-10-(aminocarbonyl)-5,8-bis(dimethylamino)-9,11a,12-trihydroxy-11,13-dioxo-6,6a,7,7a,8,11,11a,13-octahydrotetraceno[2,1-d][1,3]oxazol-2-yl]-2-furyl}methyl acetate

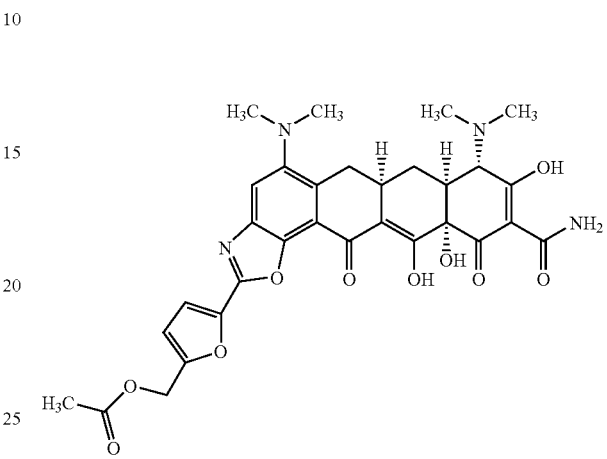

MS (ESI) m/z 621.2 (M+H);
HRMS: calcd for C$_{31}$H$_{32}$N$_4$O$_{10}$.HCl: 656.1885. found: (ESI+), 621.21807.

EXAMPLE 22

(6aR,7aS,8S,11aS)-5,8-bis(dimethylamino)-2-[(E)-2-(2-furyl)ethenyl]-9,11a,12-trihydroxy-11,13-dioxo-6,6a,7,7a,8,11,11a,13-octahydrotetraceno[2,1-d][1,3]oxazole-10-carboxamide

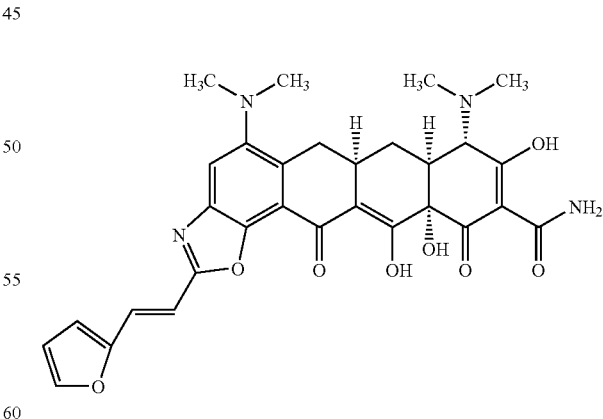

MS (ESI) m/z 575.2 (M+H); MS (ESI) m/z 288.3 (M+2H); HRMS: calcd for C$_{30}$H$_{30}$N$_4$O$_8$.HCl: 610.1830. found: (ESI–), 573.1985.

EXAMPLE 23

(6aR,7aS,8S,11aS)-2-(1-benzothien-3-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamiendtabde

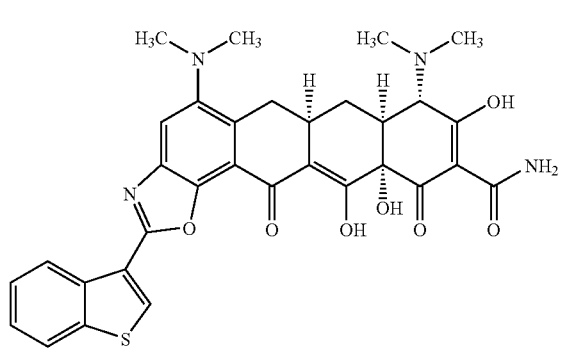

MS (ESI+) m/z 615.1 ((M+H)+); HRMS: calcd for $C_{32}H_{30}N_4O_7S \cdot HCl$: 650.1602. found: (ESI+), 615.19036.

EXAMPLE 24

(6aR,7aS,8S,11aS)-5,8-bis(dimethylamino)-9,11a,12-trihydroxy-11,13-dioxo-2-(1,3-thiazol-2-yl)-6,6a,7,7a,8,11,11a,13-octahydrotetraceno[2,1-d][1,3]oxazole-10-carboxamide

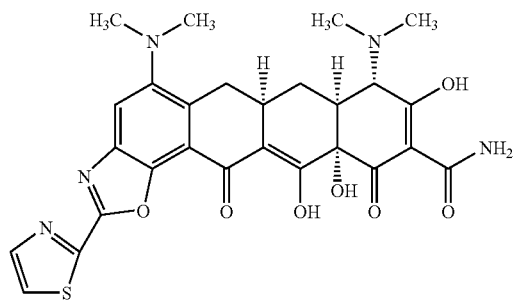

MS (ESI) m/z 566.4 (M+H); MS (ESI) m/z 283.6 (M+2H); HRMS: calcd for $C_{27}H_{27}N_5O_7S \cdot HCl$: 601.1398. found: (ESI+), 566.16973.

EXAMPLE 25

(6aR,7aS,8S,11aS)-5,8-bis(dimethylamino)-9,11a,12-trihydroxy-11,13-dioxo-2-[(E)-2-phenylethenyl]-6,6a,7,7a,8,11,11a,13-octahydrotetraceno[2,1-d][1,3]oxazole-10-carboxamide

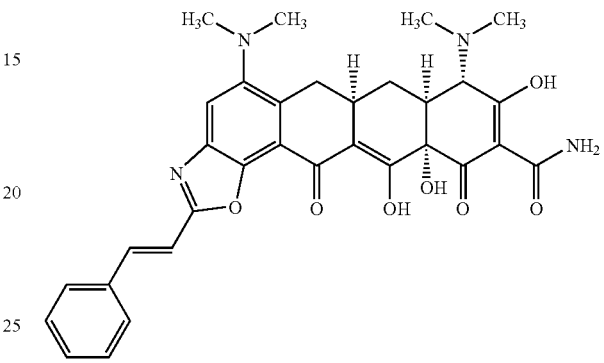

MS (ESI) m/z 585.4 (M+H); MS (ESI) m/z 293.3 (M+2H); HRMS: calcd for $C_{32}H_{32}N_4O_7 \cdot HCl$: 620.2038. found: (ESI+), 585.2329.

EXAMPLE 26

(6aR,7aS,8S,11aS)-5,8-bis(dimethylamino)-9,11a,12-trihydroxy-2-[(E)-2-(4-methoxyphenyl)ethenyl]-11,13-dioxo-6,6a,7,7a,8,11,11a,13-octahydrotetraceno[2,1-d][1,3]oxazole-10-carboxamide

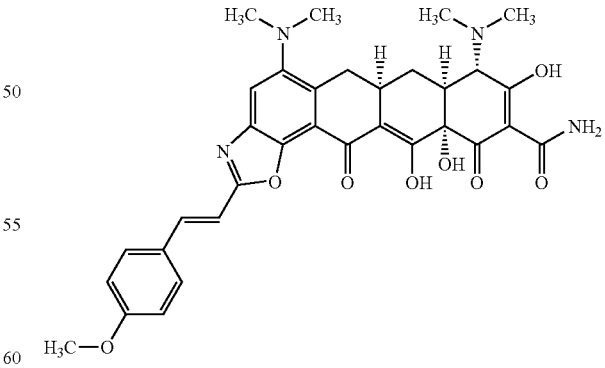

MS (ESI) m/z 615.3 (M+H); MS (ESI) m/z 308.3 (M+2H); HRMS: calcd for $C_{33}H_{34}N_4O_8 \cdot HCl$: 650.2143. found: (ESI+), 615.24413.

EXAMPLE 27

(6aR,7aS,8S,11aS)-5,8-bis(dimethylamino)-9,11a,12-trihydroxy-2-[(E)-2-(3-methoxyphenyl)ethenyl]-11,13-dioxo-6,6a,7,7a,8,11,11a,13-octahydrotetraceno[2,1-d][1,3]oxazole-10-carboxamide

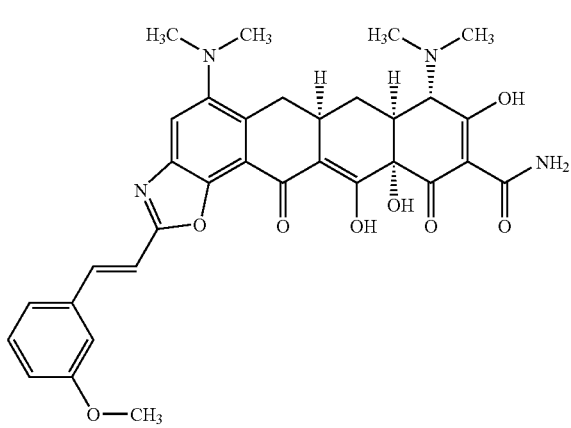

MS (ESI) m/z 615.4 (M+H); MS (ESI) m/z 308.3 (M+2H); HRMS: calcd for $C_{33}H_{34}N_4O_8 \cdot HCl$: 650.2143. found: (ESI+), 615.24419.

EXAMPLE 28

(6aR,7aS,8S,11aS)-5,8-bis(dimethylamino)-9,11a,12-trihydroxy-2-[(E)-2-(2-methoxyphenyl)ethenyl]-11,13-dioxo-6,6a,7,7a,8,11,11a,13-octahydrotetraceno[2,1-d][1,3]oxazole-10-carboxamide

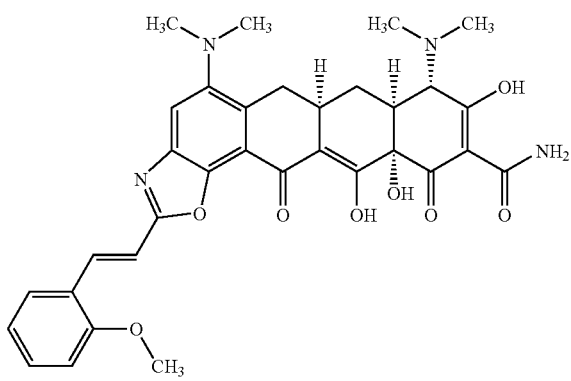

MS (ESI) m/z 615.3 (M+H); MS (ESI) m/z 308.3 (M+2H); HRMS: calcd for $C_{33}H_{34}N_4O_8 \cdot HCl$: 650.2143. found: (ESI+), 615.24408.

EXAMPLE 29

(6aR,7aS,8S,11aS)-5,8-bis(dimethylamino)-2-[(E)-2-(4-fluorophenyl)ethenyl]-9,11a,12-trihydroxy-11,13-dioxo-6,6a,7,7a,8,11,11a,13-octahydrotetraceno[2,1-d][1,3]oxazole-10-carboxamide

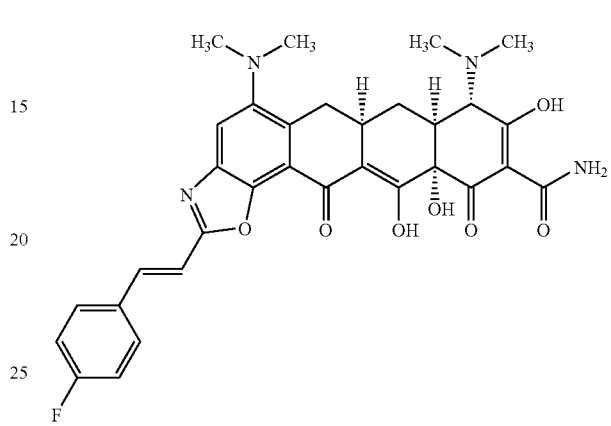

MS (ESI) m/z 603.3 (M+H); MS (ESI) m/z 302.3 (M+2H); HRMS: calcd for $C_{32}H_{31}FN_4O_7 \cdot HCl$: 638.1944. found: (ESI+), 603.22476.

EXAMPLE 30

(6aR,7aS,8S,11aS)-5,8-bis(dimethylamino)-2-[(E)-2-(2-fluorophenyl)ethenyl]-9,11a,12-trihydroxy-11,13-dioxo-6,6a,7,7a,8,11,11a,13-octahydrotetraceno[2,1-d][1,3]oxazole-10-carboxamide

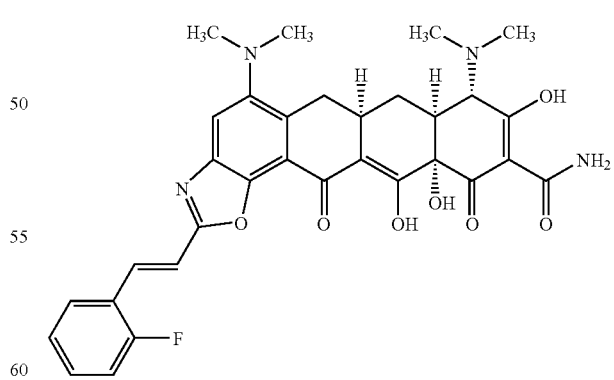

MS (ESI) m/z 603.2 (M+H); MS (ESI) m/z 302.3 (M+2H); HRMS: calcd for $C_{32}H_{31}FN_4O_7 \cdot HCl$: 638.1944. found: (ESI+), 603.22469.

EXAMPLE 31

(6aR,7aS,8S,11aS)-2-(4-tert-butylphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

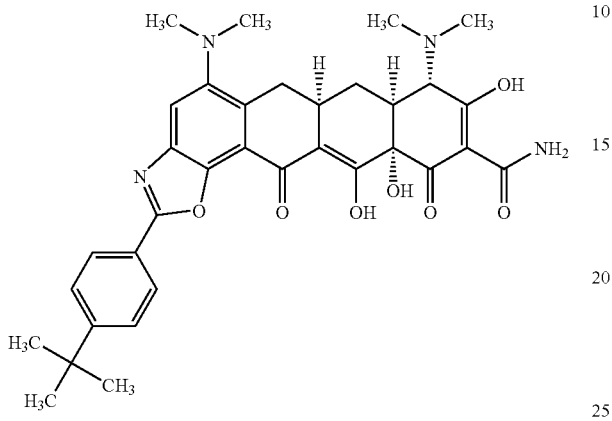

MS (ESI) m/z 615.3 (M+H); MS (ESI) m/z 308.3 (M+2H); HRMS: calcd for $C_{34}H_{38}N_4O_7 \cdot HCl$: 650.2507. found: (ESI+), 615.28057.

EXAMPLE 32

(6aR,7aS,8S,11aS)-5,8-bis(dimethylamino)-2-[4-(hexyloxy)phenyl]-9,11a,12-trihydroxy-11,13-dioxo-6,6a,7,7a,8,11,11a,13-octahydrotetraceno[2,1-d][1,3]oxazole-10-carboxamide

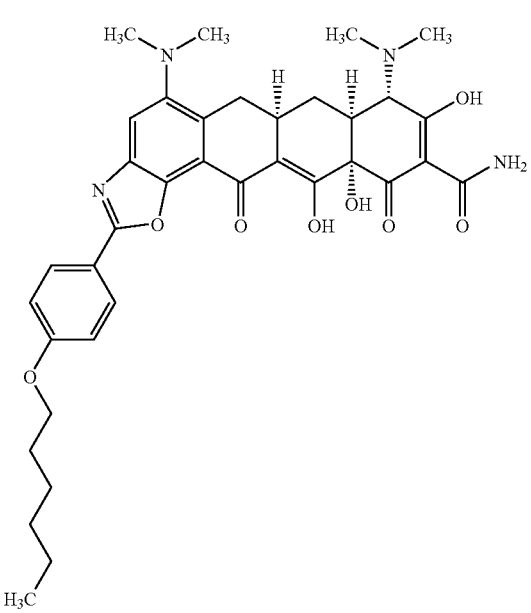

MS (ESI) m/z 659.4 (M+H); MS (ESI) m/z 330.4 (M+2H); HRMS: calcd for $C_{36}H_{42}N_4O_8 \cdot HCl$: 694.2769. found: (ESI+), 659.30693.

EXAMPLE 33

(6aR,7aS,8S,11aS)-5,8-bis(dimethylamino)-9,11a,12-trihydroxy-11,13-dioxo-2-pyridin-4-yl-6,6a,7,7a,8,11,11a,13-octahydrotetraceno[2,1-d][1,3]oxazole-10-carboxamide

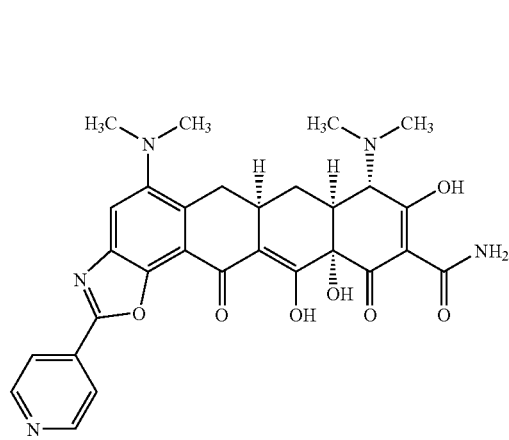

MS (ESI−) m/z 558.4 ((M−H)−);

EXAMPLE 34

(6aR,7aS,8S,11aS)-5,8-bis(dimethylamino)-9,11a,12-trihydroxy-11,13-dioxo-2-pyridin-3-yl-6,6a,7,7a,8,11,11a,13-octahydrotetraceno[2,1-d][1,3]oxazole-10-carboxamide

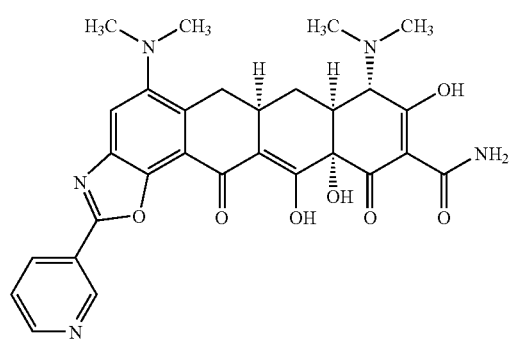

MS (ESI) m/z 560.3 (M+H); MS (ESI) m/z 280.7 (M+2H); HRMS: calcd for $C_{29}H_{29}N_5O_7 \cdot HCl$: 595.1834. found: (ESI+), 560.21353.

EXAMPLE 35

(6aR,7aS,8S,11aS)-2-(chloromethyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

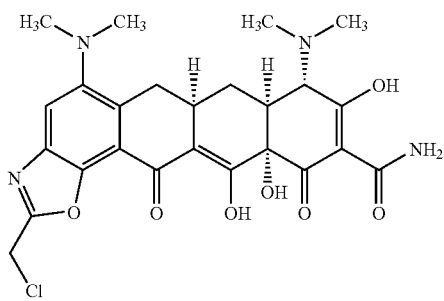

MS (ESI) m/z 531.2 (M+H); MS (ESI) m/z 266.3 (M+2H);

EXAMPLE 36

(6aR,7aS,8S,11aS)-5,8-bis(dimethylamino)-2-[(dimethylamino)methyl]-9,11a,12-trihydroxy-11,13-dioxo-6,6a,7,7a,8,11,11a,13-octahydrotetraceno[2,1-d][1,3]oxazole-10-carboxamide

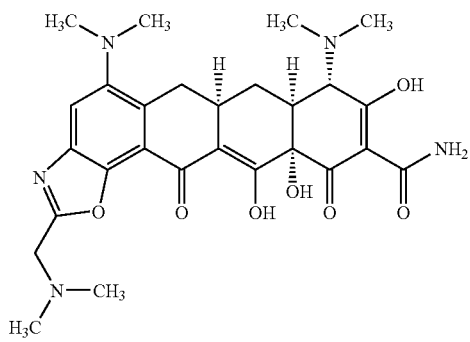

MS (ESI) m/z 540.4 (M+H); MS (ESI) m/z 270.7 (M+2H); HRMS: calcd for $C_{27}H_{33}N_5O_7 \cdot HCl$: 575.2147. found: (ESI+), 540.24506.

EXAMPLE 37

(6aR,7aS,8S,11aS)-5,8-bis(dimethylamino)-9,11a,12-trihydroxy-11,13-dioxo-2-(pyrrolidin-1-ylmethyl)-6,6a,7,7a,8,11,11a,13-octahydrotetraceno[2,1-d][1,3]oxazole-10-carboxamide

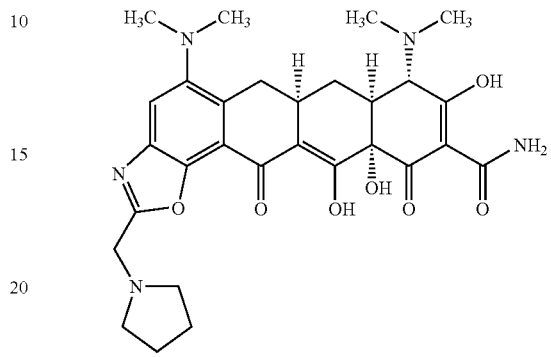

MS (ESI) m/z 566.4 (M+H); MS (ESI) m/z 283.9 (M+2H); HRMS: calcd for $C_{29}H_{35}N_5O_7 \cdot HCl$: 601.2303. found: (ESI+), 566.26066.

Example of Procedure B

EXAMPLE 38

(6aR,7aS,8S,11aS)-5,8-bis(dimethylamino)-9,11a,12-trihydroxy-11,13-dioxo-2-[(propylamino)methyl]-6,6a,7,7a,8,11,11a,13-octahydrotetraceno[2,1-d][1,3]oxazole-10-carboxamide

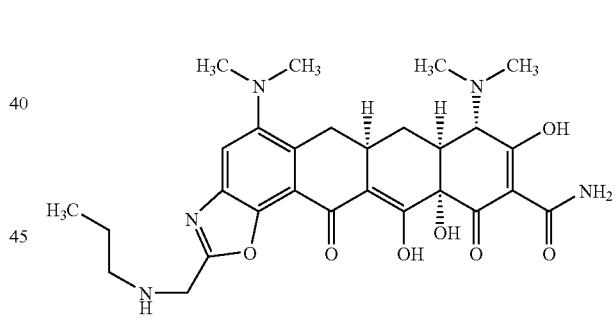

9-aminominocycline sulfate salt (1.0 g, 1.50 mmol) is dissolved in DMF (50 mL) and treated with a solution of 2-chloro-1,1,1-trimethoxyethane (0.463 g, 3.00 mmol, 2 equivalents). The reaction is stirred at room temperature until mass spectrometry shows conversion to the chloromethylbenzoxazole derivative. The solution is then treated with n-propylamine (10 mL, excess) and stirred until mass spectrometry shows conversion to the n-propylaminomethyl benzoxazole. The mixture is concentrated under reduced pressure to remove excess n-propylamine, and then poured slowly into ether (1 L) and HCl/ether is added to precipate the salt. The solid is rinsed with fresh ether and dried under vacuum. The crude solid is dissolved in water (100 mL) giving a solution at pH 2. The pH is raised successively by 0.5 units with aqueous ammonia, and extracted with dichloromethane. The fractions extracted at pH 4–4.5 are combined, dried ($Na_2SO_4$), filtered and concentrated nearly to dryness. A small volume of methanol is added and the solution is treated with 1M HCl in ether. The precipitated solid is collected by filtration, washed with fresh ether and dried under vacuum to yield 0.067 g of the product as its HCl salt.

Selected 1H NMR signals: δ 0.94 (t, 3H), 1.73 (m, 2H), 4.31 (s, 1H), 4.65 (s, 2H), 7.78 (s, 1H), 9.15 (s, 1H), 9.67 (s, 1H).

The compounds of this invention listed below in Examples 39 to 41 are prepared substantially following the method described in detail hereinabove in Example 38 using procedure B.

Prepared from Procedure B

EXAMPLE 39

(6aR,7aS,8S,11aS)-2-[(butylamino)methyl]-5,8-bis (dimethylamino)-9,11a,12-trihydroxy-11,13-dioxo-6, 6a,7,7a,8,11,11a,13-octahydrotetraceno[2,1-d][1,3] oxazole-10-carboxamide

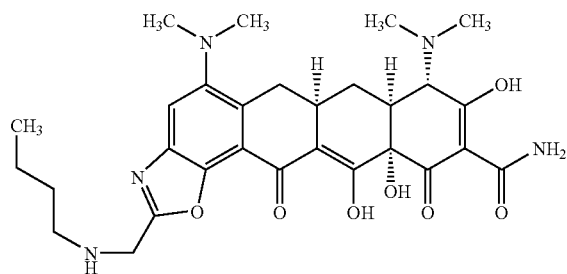

MS (ESI) m/z 568.3 (M+H); MS (ESI) m/z 284.8 (M+2H); MS (ESI) m/z 305.2 (M+ACN+2H); HRMS: calcd for $C_{29}H_{37}N_5O_7 \cdot HCl$: 603.2460. found: (ESI+), 568.27616.

Procedure B

EXAMPLE 40

(6aR,7aS,8S,11aS)-5,8-bis(dimethylamino)-9,11a, 12-trihydroxy-11,13-dioxo-2-[(propylamino)methyl]-6,6a,7,7a,8,11,11a,13-octahydrotetraceno[2,1-d][1,3]oxazole-10-carboxamide

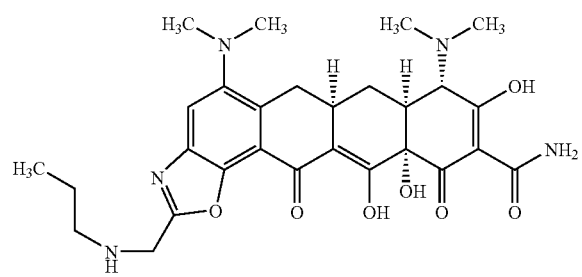

MS (ESI) m/z 554.3 (M+H); MS (ESI) m/z 277.7 (M+2H); HRMS: calcd for $C_{28}H_{35}N_5O_7 \cdot HCl$: 589.2303. found: (ESI+), 554.2604.

Procedure B

EXAMPLE 41

(6aR,7aS,8S,11aS)-2-[(tert-butylamino)methyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide

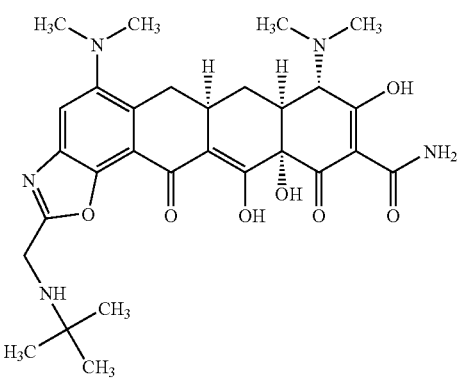

9-aminominocycline sulfate salt (1.0 g, 1.50 mmol) is dissolved DMF (20 mL) and treated with a solution of 2-chlorotrimethoxyethane (0.35 g, 2.2 mmol, 1.46 equivalents). The reaction is stirred at room temperature until mass spectrometry showed conversion to the chloromethylbenzoxazole derivative. The solution is then treated with t-butylamine (7.3 mL, excess) and stirred until mass spectrometry showed conversion to the t-butylaminomethyl benzoxazole. The mixture is concentrated under reduced pressure to remove excess t-butylamine, and then poured slowly into ether (1 L) and HCl/ether is added to precipate the salt. The solid is rinsed with fresh ether and dried under vacuum. The crude solid is dissolved in water (100 mL) giving a solution at pH 2. The pH is raised successively by 0.5 units with aqueous ammonia, and extracted with dichloromethane. The fractions extracted at pH 4–4.5 are combined, dried ($Na_2SO_4$), filtered and concentrated nearly to dryness. A small volume of methanol is added and the solution is treated with 1M HCl in ether. The precipitated solid is collected by filtration, washed with fresh ether and dried under vacuum to give the product as its HCl salt.

MS (ESI+) m/z 568.4 ((M+H)+); MS (ESI+) m/z 284.9 ((M+2H)2+); MS (ESI+) m/z 146.3 ((M'+H)+); HRMS: calcd for $C_{29}H_{37}N_5O_7 \cdot HCl$: 603.2460. found: (ESI-), 566.26087.

Example of Procedure C

EXAMPLE 42

(6aR,7aS,8S,11aS)-5,8-bis(dimethylamino)-9,11a, 12-trihydroxy-11,13-dioxo-2-thioxo-2,3,6,6a,7,7a,8, 11,11a,13-decahydrotetraceno[2,1-d][1,3]oxazole-10-carboxamide

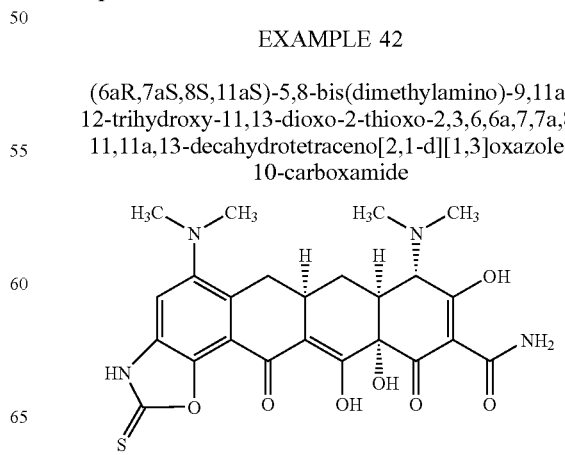

To a solution of 9-amino-mino disulfate (0.668 g, 1 mmol) in DMSO (30 mL) is added 2 equivalents of 1,1-thiocarbonyldiimidazole. The reaction is then stirred at room temperature for 2 to 12 hr (followed by MS(ES)). The mixture then triturated with diethyl ether and the solid collected. Material is used in the next step without further purification.

MS (ESI) m/z 515.2 (M+H); HRMS: calcd for $C_{24}H_{26}N_4O_7S \cdot H_2SO_4$: 612.1196. found: (ESI+), 515.15934.

The compounds of this invention listed below in Examples 43 to 44 are prepared substantially following the method described in detail hereinabove in Example 42 using procedure C.

Example of Procedure C

Procedure C

EXAMPLE 43 benzyl {[(6aR,7aS,8S,11aS)-10-(aminocarbonyl)-5,8-bis(dimethylamino)-9,11a,12-trihydroxy-11,13-dioxo-6,6a,7,7a,8,11,11a,13-octahydrotetraceno[2,1-d][1,3]oxazol-2-yl]thio}acetate

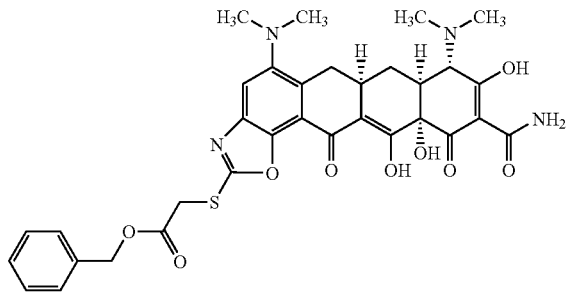

To a solution of (6aR,7aS,8S,11aS)-5,8-bis(dimethylamino)-9,11a,12-trihydroxy-11,13-dioxo-2-thioxo-2,3,6,6a,7,7a,8,11,11a,13-decahydrotetraceno[2,1-d][1,3]oxazole-10-carboxamide (Example 42) in N,N-dimethylformamide (DMF) is added 2 equivalents of diisopropylethylamine, after stirring for 5 min. 1.2 equivalent of benzyl-2-bromoacetate is added. The reaction mixture is stirred for 1 hr and mixture triturated with diethyl ether and solid is collected. It is purified by extraction.

MS (ESI) m/z 663.2 (M+H); MS (ESI) m/z 332.1 (M+2H); HRMS: calcd for $C_{33}H_{34}N_4O_9S \cdot HCl$: 698.1813. found: (ESI+), 663.2115.

EXAMPLE 44

(6aR,7aS,8S,11aS)-5,8-bis(dimethylamino)-2-[(4-fluorobenzyl)thio]-9,11a,12-trihydroxy-11,13-dioxo-6,6a,7,7a,8,11,11a,13-octahydrotetraceno[2,1-d][1,3]oxazole-10-carboxamide

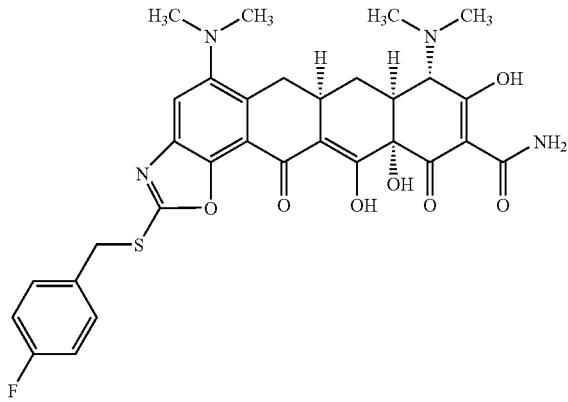

The compound of the example is prepared using procedure D in Example 43 using 4-fluorobenzylbromide.

MS (ESI) m/z 622.9 (M+H); HRMS: calcd for $C_{31}H_{31}FN_4O_7S \cdot HCl$: 658.1664. found: (ESI+), 623.19689.

Example of Procedure D (Compound 1 to 4 to 6)

EXAMPLE 45

[4S-(4α,4aα,5aα,12aα)]-4,7-Bis(dimethylamino)-9-[2-(1,1-dimethylethylamino)acetylamino]-1,4,4a,5,5a,6,11,12a-octahydro-3,10,12,12a-tetrahydroxy-1,11-dioxo-2-naphthacenecarboxamide mono HCl; free base

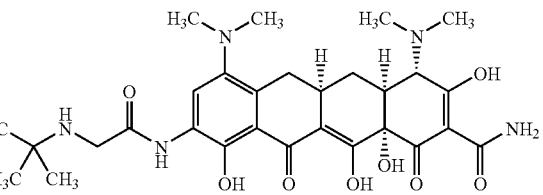

9-aminominocycline sulfate salt (1.0 g, 1.50 mmol) is dissolved DMF (20 mL) and treated with a solution of 2-chlorotrimethoxyethane (0.35 g, 2.2 mmol, 1.47 equivalents). The reaction is stirred at room temperature until mass spectrometry showed conversion to the chloromethylbenzoxazole derivative. The solution is then treated with t-butylamine (7.3 mL, excess) and stirred until mass spectrometry showed conversion to the t-butylaminomethyl benzoxazole. The mixture is concentrated under reduced pressure to remove excess t-butylamine, and then poured slowly into ether (1 L) and HCl/ether is added to precipitate the salt. The solid is rinsed with fresh ether and dried under vacuum. The crude solid is dissolved in water (100 mL) giving a solution at pH 2. The pH is raised successively by 0.5 units with aqueous ammonia, and extracted with dichloromethane. The fractions extracted at pH 4–4.5 are combined, dried ($Na_2SO_4$), filtered and concentrated nearly to dryness. A small volume of methanol is added and the solution is treated with 1M HCl in ether. The precipitated solid is collected by filtration, washed with fresh ether and dried under vacuum to give the product as its HCl salt.

Product from example 41 is treated with aqueous acid for one hour to 24 hour to give mono HCL salt of example 45

MS (ESI+) m/z 586.4 ((M+H)+;

The following examples are prepared using similar method described in procedure D.

EXAMPLE 46

[4S-(4α,4aα,5aα,12aα)]-4,7-Bis(dimethylamino)-9-[(dimethyamino)acetylamino]-1,4,4a,5,5a,6,11,12a-octahydro-3,10,12,12a-tetrahydroxy-1,11-dioxo-2-naphthacenecarboxamide

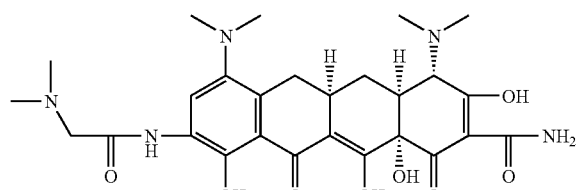

MS (FAB) m/z 558 ((M+H)+;

EXAMPLE 47

[4S-(4α,4aα,5aα,12aα)]-4,7-Bis(dimethylamino)-9-
[[(n-butylamino)acetyl]amino]-1,4,4a,5,5a,6,11,12a-
octahydro-3,10,12,12a-tetrahydroxy-1,11-dioxo-2-
naphthacenecarboxamide

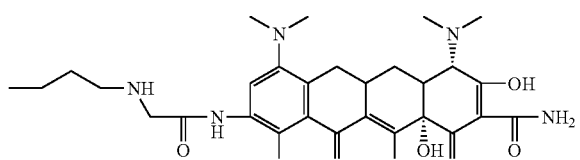

MS (FAB) m/z 586 ((M+H)+;

EXAMPLE 48

[4S-(4α,4aα,5aα,12aα)]-4,7-Bis(dimethylamino)-9-
[[(propylamino)acetyl]amino]-1,4,4a,5,5a,6,11,12a-
octahydro-3,10,12,12a-tetrahydroxy-1,11-dioxo-2-
naphthacenecarboxamide

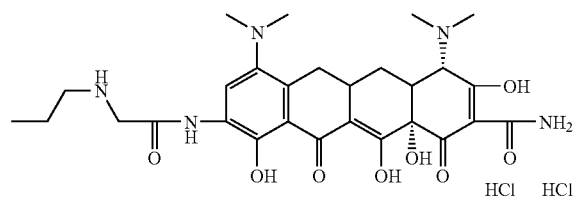

MS (FAB) m/z 572 ((M+H)+;

EXAMPLE 49

[4S-(4α,4aα,5aα,12aα)]-4,7-Bis(dimethylamino)-9-
[(chloroacetyl)amino]-1,4,4a,5,5a,6,11,12a-octahy-
dro-3,10,12,12a-tetrahydroxy-1,11-dioxo-2-naph-
thacenecarboxamide

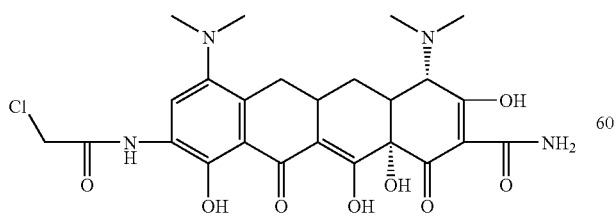

MS (FAB) m/z 549 ((M+H)+;

What is claimed is:
1. A compound of Formula (I);

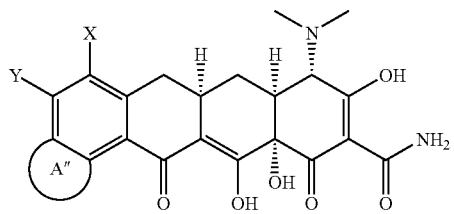

wherein:
X is selected from hydrogen, amino, $NR^{11}R^{12}$, alkyl of 1 to 12 carbon atoms optionally substituted, aryl of 6, 10 or 14 carbon atoms optionally substituted, vinyl optionally substituted, alkynyl of 2 to 12 carbon atoms optionally substituted and halogen;

A″ is a moiety selected from the group:

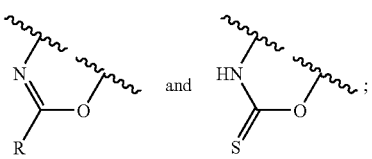

$R^{11}$ and $R^{12}$ are each independently H or alkyl of 1 to 12 carbon atoms or $R^{11}$ and $R^{12}$ when optionally taken together with the nitrogen atom to which each is attached form a 3 to 7 membered saturated hydrocarbon ring;

Y is selected from hydrogen, alkyl of 1 to 12 carbon atoms optionally substituted, aryl of 6, 10 or 14 carbon atoms optionally substituted, alkenyl of 2 to 12 carbon atoms optionally substituted, vinyl, alkynyl of 2 to 12 carbon atoms optionally substituted and halogen;

R is selected from alkyl of 1 to 12 carbon atoms optionally substituted, alkenyl of 2 to 6 carbon atoms optionally substituted, alkynyl of 2 to 12 carbon atoms optionally substituted, —$CH_2NR^1R^2$, aryl of 6, 10 or 14 carbon atoms optionally substituted, aralkyl of 7 to 16 carbon atoms optionally substituted, aroyl of 7 to 13 carbon atoms optionally substituted, $SR^3$, heteroaryl of 5 or 6 ring atoms optionally substituted, containing 1 to 4 heteroatoms which may be the same or different, independently selected from nitrogen, oxygen and sulfur, and heteroarylcarbonyl of 5 or 6 ring atoms optionally substituted containing 1 to 4 heteroatoms which may be the same or different, independently selected from nitrogen, oxygen and sulfur;

$R^1$ and $R^2$ are each independently H or alkyl of 1 to 12 carbon atoms or $R^1$ and $R^2$ when optionally taken together with the nitrogen atom to which each is attached form a 3 to 7 membered saturated hydrocarbon ring;

$R^3$ is alkyl of 1 to 12 carbon atoms optionally substituted, —$CH_2$-aryl optionally substituted, aralkyl of 7 to 16 carbon atoms optionally substituted, aroyl, —$CH_2(CO)$ $OCH_2$aryl optionally substituted, —$CH_2$-alkenyl of 2 to 12 carbon atoms optionally substituted, and —$CH_2$-alkynyl of 2 to 12 carbon atoms optionally substituted;

with the proviso that when X is $NR^{11}R^{12}$ and $R^{11}$ is hydrogen, then $R^{12}$ is methyl, ethyl, n-propyl, n-butyl, 1-methylethyl, 1-methylpropyl, 2-methylpropyl or 1,1-dimethylethyl; and that when $R^{11}$ is methyl or ethyl then $R^{12}$ is methyl, ethyl, n-propyl, 1-methylethyl, n-propyl, 1-methylpropyl, or 2-methylpropyl;

or a tautomer or a pharmaceutically acceptable salt thereof.

2. A compound according to claim 1 wherein R is phenyl optionally substituted with 1 to 3 substituents or a pharmaceutically acceptable salt thereof.

3. A compound according to claim 1 wherein R of Formula (I) is selected from the group alkyl of 1 to 6 carbon atoms, alkenyl of 2 to 6 carbon atoms, and alkyl-heterocyclyl or a pharmaceutically acceptable salt thereof.

4. A compound according to claim 3 wherein alkyl-heterocyclyl is selected from moieties of the group

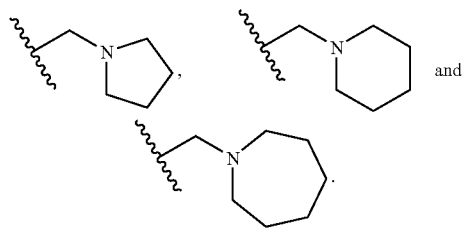

or a pharmaceutically acceptable salt thereof.

5. A compound according to claim 2 wherein R is selected from moieties of the group

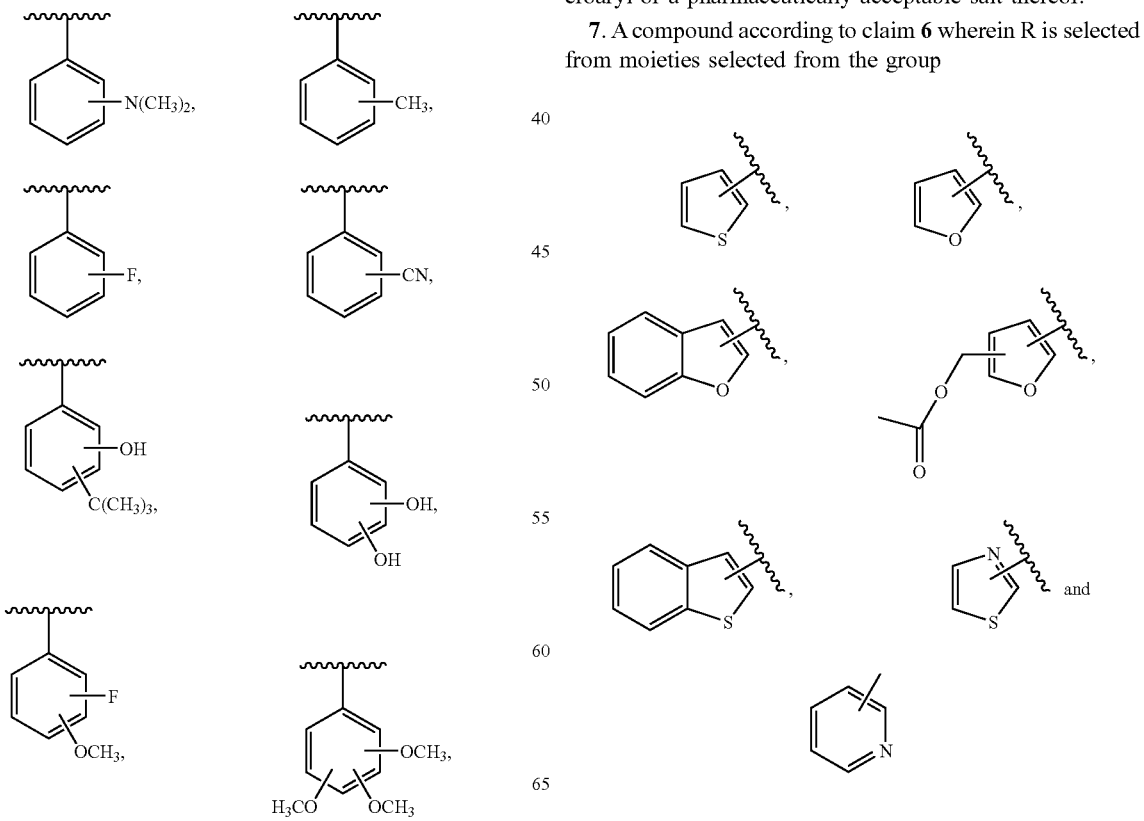

or a pharmaceutically acceptable salt thereof.

6. A compound according to claim 1 wherein R is heteroaryl or a pharmaceutically acceptable salt thereof.

7. A compound according to claim 6 wherein R is selected from moieties selected from the group

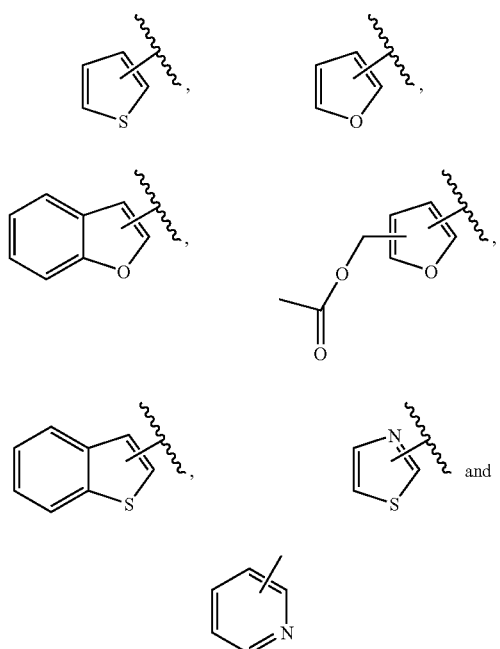

or a pharmaceutically acceptable salt thereof.

8. A compound according to claim 1 wherein R is alkyl of 1 to 6 carbon atoms optionally substituted, alkenyl of 2 to 6 carbon atoms optionally substituted,

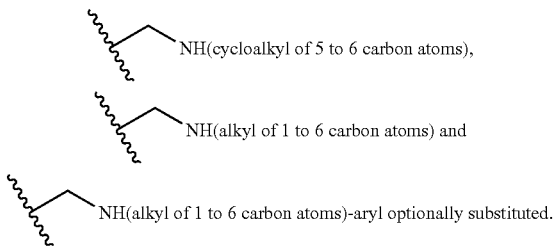

or a pharmaceutically acceptable salt thereof.

9. A compound according to claim 1 wherein R is selected from moieties

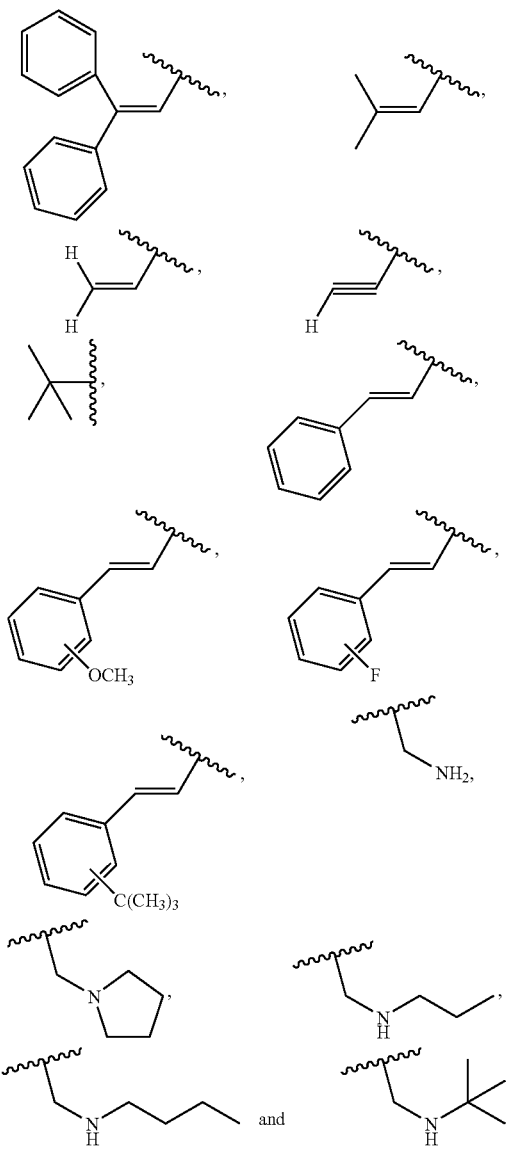

or a pharmaceutically acceptable salt thereof.

10. A compound according to claim 1 wherein R is S-alkyl of 1 to 12 carbon atoms, S—CH$_2$-aryl optionally substituted and S—CH$_2$(CO)OCH$_2$aryl optionally substituted or a pharmaceutically acceptable salt thereof.

11. A compound according to claim 10 wherein R is selected from moieties of the group

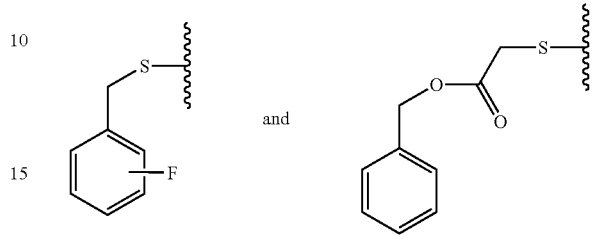

or a pharmaceutically acceptable salt thereof.

12. A compound according to claim 1 wherein Y is H.

13. A compound according to claim 1 wherein X is —NMe$_2$.

14. A compound according to claim 1 selected from the group:

(6aR,7aS,8S,11aS)-5,8-bis(dimethylamino)-2-(2,2-diphenylvinyl)-9,11a,12-trihydroxy-11,13-dioxo-6,6a,7,7a,8,11,11a,13-octahydrotetraceno[2,1-d][1,3]oxazole-10-carboxamide, (7aS,8S,11aS)-8-(dimethylamino)-9,11a,13-trihydroxy-2-(2-methyl-1-propenyl)-11,12-dioxo-7,7a,8,11,11a,12-hexahydronaphthaceno[2,1-d][1,3]oxazole-10-carboxamide, (6aR,7aS,8S,11aS)-2-tert-butyl-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-[(E)-2-(2-furyl)ethenyl]-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-[(E)-2-phenylethenyl]-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-2-[(E)-2-(4-methoxyphenyl)ethenyl]-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-2-[(E)-2-(3-methoxyphenyl)ethenyl]-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-2-[(E)-2-(2-methoxyphenyl)ethenyl]-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-[(E)-2-(4-fluorophenyl)ethenyl]-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-[(E)-2-(2-fluorophenyl)ethenyl]-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-2-(chloromethyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-[(dimethylamino)methyl]-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-(pyrrolidin-1-ylmethyl)-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-[(propylamino)methyl]-6,6a,7,7a,8,11,11a,13-octahydrotetraceno[2,1-d][1,3]oxazole-10-carboxamide, (6aR,7aS,8S,11aS)-2-[(butylamino)methyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-[(propylamino)methyl]-6,6a,7,7a,8,11,11a,13-octahydrotetraceno[2,1-d][1,3]oxazole-10-carboxamide and (6aR,7aS,8S,11aS)-2-[(tert-butylamino)methyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide; or a pharmaceutically acceptable salt thereof.

15. A compound according to claim 1 selected from the group:

(7aS,8S,11aS)-8-(dimethylamino)-2-[4-(dimethylamino)phenyl]-9,11a,13-trihydroxy-11,12-dioxo-7,7a,8,11,11a,12-hexahydronaphthaceno[2,1-d][1,3]oxazole-10-carboxamide, (6aR,7aS,8S,11aS)-2-tert-butyl-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-2-(4-methylphenyl)-11,13-dioxo-6,6a,7,7a,8,11,11a,13-octahydrotetraceno[2,1-d][1,3]oxazole-10-carboxamide, (7aS,8S,11aS)-5,8-bis(dimethylamino)-2-(3-fluorophenyl)-9,11a,13-trihydroxy-11,12-dioxo-7,7a,8,11,11a,12-hexahydrotetraceno[2,1-d][1,3]oxazole-10-carboxamide, (6aR,7aS,8S,11aS)-2-(4-cyanophenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-[4-(dimethylamino)phenyl]-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-2-(5-tert-butyl-2-hydroxyphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-2-[4-(benzyloxy)phenyl]-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-2-(2,4-dihydroxyphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-(3-fluoro-4-methoxyphenyl)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-2-(1,3-benzodioxol-5-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-(2,4,6-trimethoxyphenyl)-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-(2,4,5-triethoxyphenyl)-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-2-(1-methyl-1H-indol-2-yl)-11,13-dioxo-6,6a,7,7a,8,11,11a,13-octahydrotetraceno[2,1-d][1,3]oxazole-10-carboxamide, (6aR,7aS,8S,11aS)-2-(4-tert-butylphenyl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide and (6aR,7aS,8S,11aS)-5,8-bis(dimethylamino)-2-[4-(hexyloxy)phenyl]-9,11a,12-trihydroxy-11,13-dioxo-6,6a,7,7a,8,11,11a,13-octahydrotetraceno[2,1-d][1,3]oxazole-10-carboxamide or a pharmaceutically acceptable salt thereof.

16. A compound according to claim 1 selected from the group:

(6aR,7aS,8S,11aS)-5,8-bis(dimethylamino)-9,11a,12-trihydroxy-11,13-dioxo-2-thien-3-yl-6,6a,7,7a,8,11,11a,13-octahydrotetraceno[2,1-d][1,3]oxazole-10-carboxamide, (6aR,7aS,8S,11aS)-2-(1-benzofuran-2-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-2-(2-furyl)-9,11a,12-trihydroxy-11,13-dioxo-6,6a,7,7a,8,11,11a,13-octahydrotetraceno[2,1-d][1,3]oxazole-10-carboxamide, {5-[(6aR,7aS,8S,11aS)-10-(aminocarbonyl)-5,8-bis(dimethylamino)-9,11a,12-trihydroxy-11,13-dioxo-6,6a,7,7a,8,11,11a,13-octahydrotetraceno[2,1-d][1,3]oxazol-2-yl]-2-furyl}methyl acetate, (6aR,7aS,8S,11aS)-2-(1-benzothien-3-yl)-5,8-bis(dimethylamino)-9,11a,12-trihydroxy-11,13-dioxo-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-(1,3-thiazol-2-yl)-6,6a,7,7a,8,11,11a,13-octahydrotetraceno[2,1-d][1,3]oxazole-10-carboxamide, (6aR,7aS,8S,11aS)-5,8-bis(dimethylamino)-9,11a,12-trihydroxy-11,13-dioxo-2-pyridin-4-yl-6,6a,7,7a,8,11,11a,13-octahydrotetraceno[2,1-d][1,3]oxazole-10-carboxamide and (6aR,7aS,8S,11aS)-5,8-bis(dimethylamino)-9,11a,12-trihydroxy-11,13-dioxo-2-pyridin-3-yl-6,6a,7,7a,8,11,11a,13-octahydrotetraceno[2,1-d][1,3]oxazole-10-carboxamide or a pharmaceutically acceptable salt thereof.

17. A pharmaceutical composition comprising a compound according to claim 1 or a pharmaceutically acceptable salt thereof in association with a pharmaceutically acceptable carrier.

* * * * *